(12) United States Patent
Ichikawa et al.

(10) Patent No.: US 11,384,121 B2
(45) Date of Patent: Jul. 12, 2022

(54) CREATION OF PEPTIDE-BASED ANTI-TUMOR AGENT

(71) Applicant: National University Corporation Hokkaido University, Sapporo (JP)

(72) Inventors: Satoshi Ichikawa, Hokkaido (JP);
Keita Kojima, Hokkaido (JP);
Mikihiro Fujiya, Hokkaido (JP);
Hiroaki Konishi, Hokkaido (JP)

(73) Assignee: National University Corporation Hokkaido University, Hokkaido (JP)

( * ) Notice: Subject to any disclaimer, the term of this patent is extended or adjusted under 35 U.S.C. 154(b) by 0 days.

(21) Appl. No.: 16/963,949

(22) PCT Filed: Jan. 31, 2019

(86) PCT No.: PCT/JP2019/003482
§ 371 (c)(1),
(2) Date: Jul. 22, 2020

(87) PCT Pub. No.: WO2019/151439
PCT Pub. Date: Aug. 8, 2019

(65) Prior Publication Data
US 2021/0017232 A1 Jan. 21, 2021

(30) Foreign Application Priority Data
Jan. 31, 2018 (JP) .............................. JP2018-015606

(51) Int. Cl.
*A61K 38/00* (2006.01)
*C07K 11/02* (2006.01)
*A61P 35/00* (2006.01)

(52) U.S. Cl.
CPC .............. *C07K 11/02* (2013.01); *A61P 35/00* (2018.01); *A61K 38/00* (2013.01)

(58) Field of Classification Search
CPC ......... A61K 38/00; A61K 38/12; A61P 35/00; C07K 11/02; Y02P 20/55
See application file for complete search history.

(56) References Cited

U.S. PATENT DOCUMENTS

2009/0053769 A1  2/2009  Wang et al.

OTHER PUBLICATIONS

Alshaer et al. RSC Adv., 2019, 9, 30976.Encapsulation of echinomycin in cyclodextrin inclusion complexes into liposomes: in vitro antiproliferative and anti-invasive activity in glioblastoma (Year: 2019).*
Wigerup et al. Pharmacology & Therapeutics 164 (2016) 152-169. Therapeutic targeting of hypoxia and hypoxia-inducible factors in cancer (Year: 2016).*
Thomas et al. Cancers 2020, 12, 2279. Actively Targeted Nanodelivery of Echinomycin Induces Autophagy-Mediated Death in Chemoresistant Pancreatic Cancer In Vivo. (Year: 2020).*
Medical news today—Accessed May 8, 2020—Christina Chun, 2018 (Year: 2018).*
Robert Gale; Merck Manual accessed May 8, 2020. Overview of Cancer Therapy. (Year: 2018).*
Robert Gale; Merck Manual accessed May 8, 2020. Cancer treatment principles (Year: 2018).*
National Cancer Institute; accessed May 8, 2020. Cancer Prevention Overview (Year: 2020).*
National Cancer Institute; accessed May 8, 2020. What is Cancer? (Year: 2015).*
Hattori et al., "Solution-phase synthesis and biological evaluation of triostin A and its analogues," Organic & Biomolecular Chemistry, Jan. 7, 2016, 14(6):2090-2111.
International Search Report dated Feb. 26, 2019, in PCT/JP2019/003482.
Kim et al., "Synthesis and biological activity of new quinoxaline antibodies of echinomycin analogues," Bioorganic & Medicinal Chemistry Letters, 2004, 14:541-544.
Kong et al., "Echinomycin, a Small-Molecule Inhibitor of Hypoxia-Inducible Factor-1 DNA-Binding Activity," Cancer Research, Oct. 2005, 65(19):9047-9055.
Ponnurangam et al., "Quinomycin A targets Notch signaling pathway in pancreatic cancer stem cells," Octotarget, Dec. 11, 2015, 7(3):3217-3232.
Wadler et al., Phase II trial of echinomycin in patients with advanced or recurrent colorectal cancer, Cancer Chemother. Pharmacol., May 1994, 34(3):266-269.
Wang et al., "Echinomycin protects mice against relapsed acute myeloid leukemia without adverse effect on hematopoietic stem cells," Blood, Aug. 14, 2014, 124(7):1127-1135.
Hayakawa et al., "Quinomycins H1 and H2, new cytotoxic antibiotics from *Streptomyces* sp. RAL404," The Journal of Antibiotics, Jul. 17, 2018, 71 (10):898-901.
Supplementary European Search Report dated Oct. 20, 2021 in EP 19747665.8.
Watanabe et al., "Diversification of echinomycin molecular structure by way of chemoenzymatic synthesis and heterologous expression of the engineered echinomycin biosynthetic pathway," Current opinion in Chemical Biology, Apr. 1, 2009, 13(2): 189-196.

* cited by examiner

*Primary Examiner* — Aradhana Sasan
*Assistant Examiner* — Mercy H Sabila
(74) *Attorney, Agent, or Firm* — Foley & Lardner LLP

(57) ABSTRACT

An object of the present invention is to provide an echinomycin derivative that has anti-cancer activity equal to or greater than that of echinomycin, and a production method therefor based on a chemical procedure. Provided are an echinomycin derivative represented by formula (I), and a production method therefor based on a chemical procedure.

12 Claims, 7 Drawing Sheets

CREATION OF PEPTIDE-BASED ANTI-TUMOR AGENT

CROSS-REFERENCE TO RELATED APPLICATIONS

This application is the U.S. National Stage of PCT/JP2019/003482, filed Jan. 31, 2019, which claims priority to JP 2018-015606, filed Jan. 31, 2018.

TECHNICAL FIELD

The present invention relates to an echinomycin derivative and a production method therefor, and a pharmaceutical composition for treating cancer, the pharmaceutical composition containing an echinomycin derivative as an active ingredient.

BACKGROUND ART

Cancer has been the first cause of death for the Japanese since 1981 until today, and novel therapeutic methods therefor have been constantly demanded. Examples of therapeutic methods for cancer include surgical therapy, radiotherapy, and chemotherapy (anti-cancer agents), and anti-cancer agents are especially widely used through combined application with other therapy. While alkylating agents, antimetabolites, alkaloidal anti-cancer agents, antibiotic anti-cancer agents, platinum formulations, and so on are used as anti-cancer agents, therapeutic effects of them are still insufficient, and moreover they disadvantageously cause frequent occurrence of adverse effects. Thus, development of superior anti-cancer agents is desired.

Echinomycin is a cyclic-peptide-type natural product isolated from the actinomycete *Streptomyces echinatus* in 1957. Echinomycin has been confirmed to exhibit potent anti-cancer activity in vitro and in vivo. In the United States, a phase 2 clinical trial was conducted for an anti-cancer agent containing echinomycin as an active ingredient (Non Patent Literature 1) and found its toxicity. For this reason, subsequent clinical development was abandoned.

However, echinomycin was recently revealed to have HIF-1a inhibitory activity (Non Patent Literature 2), and it was reported that echinomycin administered in a low dose exhibits cell-growth-suppressing activity selectively on cancer stem cells, thus being effective for treatment of pancreatic cancer, acute myeloid leukemia, and so on (Non Patent Literature 3, Non Patent Literature 4). Therefore, echinomycin is again attracting attention, and resumption of clinical trial with dose control is currently under consideration.

On the other hand, production of echinomycin depends on procedures based on biosynthesis by microorganisms, and no chemical production method has been developed. A method of chemically modifying echinomycin obtained from microorganisms is known, whereas echinomycin derivatives previously synthesized all have lower anti-cancer activity than echinomycin.

CITATION LIST

Non Patent Literature

Non Patent Literature 1: Cancer Chemother. Pharmacol. 1994, 34, 266-269.
Non Patent Literature 2: Cancer Res. 2005, 19, 99047-9055.
Non Patent Literature 3: Oncotarget. 2016 Jan. 19; 7(3): 3217-32.
Non Patent Literature 4: Blood. 2014 Aug. 14; 124(7): 1127-1135.

SUMMARY OF INVENTION

Technical Problem

An object of the present invention is to provide an echinomycin derivative that has anti-cancer activity equal to or greater than that of echinomycin, and a production method therefor based on a chemical procedure.

Solution to Problem

The present inventors found that the thioacetal site in the chemical structure of echinomycin is not required for development of anti-cancer activity, and an echinomycin derivative removed of the site can be easily produced on the basis of a chemical procedure, and further found that the echinomycin derivative thus obtained has anti-cancer activity equal to or greater than that of echinomycin.

The present invention is based on these findings, and includes the following inventions.

[1] A compound or a salt thereof, the compound represented by formula (I):

[Formula 1]

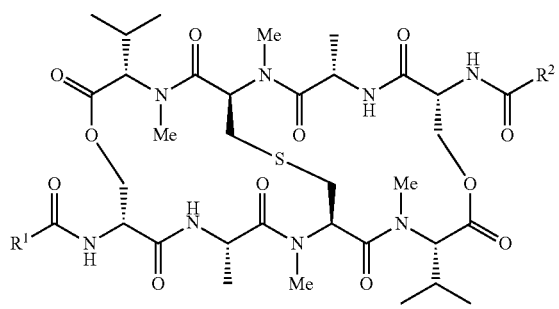

wherein $R^1$ and $R^2$ are each independently selectable and identical or different, and each represent an aromatic hydrocarbon group, saturated or unsaturated heterocyclic group, anthraquinone group, or benzophenone group optionally substituted with one or more substituents.

[2] The compound or salt thereof according to [1], wherein $R^1$ and $R^2$ are each independently selectable and identical or different, and are each a group selected from a quinolyl group, an isoquinolyl group, a quinazolinyl group, a quinoxalyl group, a cinnolyl group, an indolyl group, a benzofuranyl group, a benzothiazolyl group, a benzoxazolyl group, a benzothiophene group, a pyrazyl group, an anthraquinone group, and a benzophenone group, and optionally substituted with one or more substituents selected from the group consisting of a hydrogen atom, a halogen atom, a hydroxy group, and a $C_{1-6}$ alkyl group.

[3] The compound or salt thereof according to [1] or [2], wherein the compound is represented by formula (II):

[Formula 2]

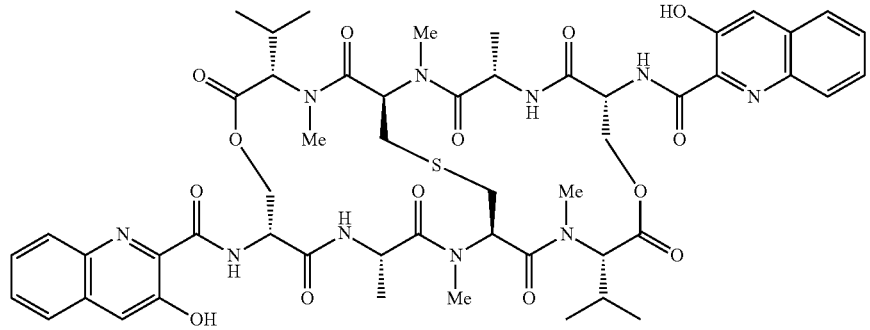

or formula (III):

[Formula 3]

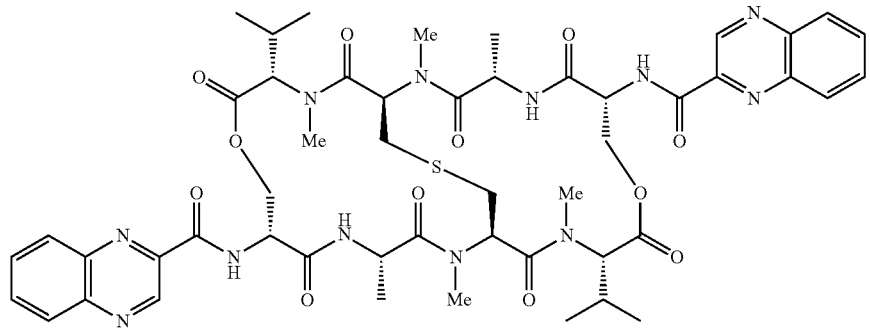

[4] A pharmaceutical composition for treating cancer, the pharmaceutical composition containing the compound or salt thereof according to any one of [1] to [3].

[5] A method for producing the compound according to any one of [1] to [3], the method including:

a step of producing the compound represented by formula (I) from a compound represented by formula (6):

[Formula 4]

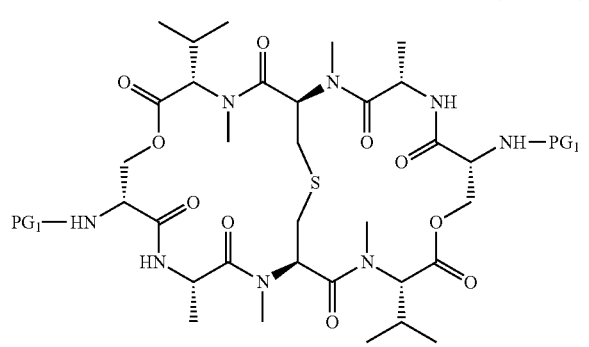

(Formula 6)

wherein $PG_1$ represents a protective group for an amino group, and compounds represented by formula (7):

[Formula 5]

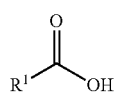

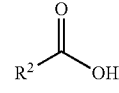

(Formula 7)

wherein $R^1$ and $R^2$ are each independently selectable and identical or different, and each represent an aromatic hydrocarbon group, saturated or unsaturated heterocyclic group, anthraquinone group, or benzophenone group optionally substituted with one or more substituents.

[6] The method according to [5], wherein the compound represented by formula (6) is produced by reacting a compound represented by formula (3):

[Formula 6]

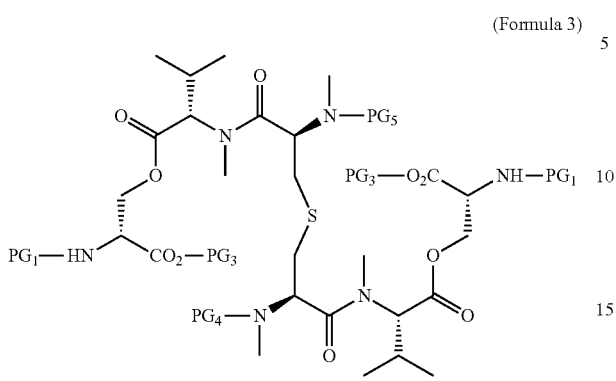

(Formula 3)

wherein $PG_1$ represents a protective group for an amino group, $PG_3$ represents a protective group for a carboxy group, and $PG_4$ and $PG_5$ are identical or different and each represent a protective group for an amino group, provided that $PG_4$ and $PG_5$ are different from $PG_1$, and a compound represented by formula (4):

[Formula 7]

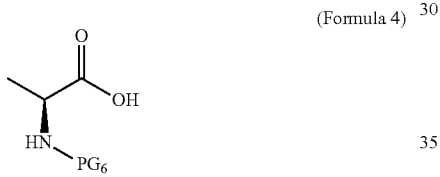

(Formula 4)

wherein $PG_6$ represents a protective group for an amino group, provided that $PG_6$ is different from $PG_1$, to produce a compound represented by formula (5):

[Formula 8]

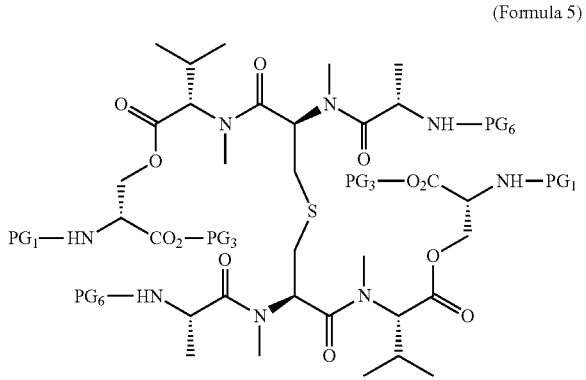

(Formula 5)

wherein $PG_1$, $PG_6$, and $PG_3$ are as defined above, and producing the compound represented by formula (6) from the obtained compound represented by formula (5).

[7] The method according to [6], wherein the compound represented by formula (3) is produced from a compound represented by formula (1):

[Formula 9]

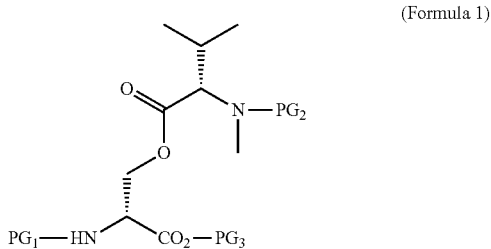

(Formula 1)

wherein $PG_1$ represents a protective group for an amino group, $PG_2$ represents a protective group for an amino group, provided that $PG_2$ is different from $PG_1$, and $PG_3$ represents a protective group for a carboxy group, and a compound represented by formula (2):

[Formula 10]

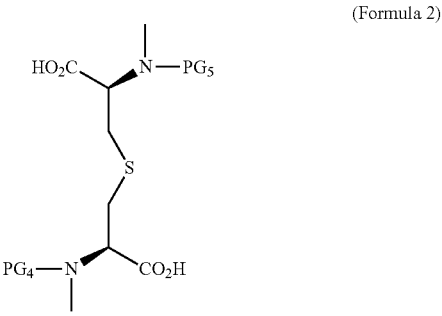

(Formula 2)

wherein $PG_4$ and $PG_5$ are identical or different and each represent a protective group for an amino group, provided that $PG_4$ and $PG_5$ are different from $PG_1$.

[8] A method for treating cancer, the method including administering the compound or salt thereof according to any one of [1] to [3] to a cancer patient.

[9] The compound or salt thereof according to any one of [1] to [3] for use in a method for treating cancer.

[10] Use of the compound or salt thereof according to any one of [1] to [3] in production of a drug for treating cancer.

The present specification includes the contents of the specification and/or drawings of Japanese Patent Application No. 2018-015606, which is a priority document of the present application.

All publications, patents, and patent applications cited herein are totally incorporated herein by reference.

Advantageous Effects of Invention

The present invention can provide an echinomycin derivative that has anti-cancer activity equal to or greater than that of echinomycin, and a production method therefor based on a chemical procedure.

BRIEF DESCRIPTION OF DRAWINGS

FIG. 1-2 shows a graph representing results of evaluation on the anti-cancer activity of the compound of the present invention through SRB assay with use of a pancreatic cancer cell (SuiT-2 cell) line. *: p<0.05 (vs control, Student's t-test)

FIG. 1-3 shows a graph representing results of evaluation on the anti-cancer activity of the compound of the present invention through SRB assay with use of a colorectal cancer cell (SW620 cell) line. *: p<0.05 (vs control, Student's t-test)

FIG. 2-1 shows graphs representing results of evaluation on the anti-cancer activity of the compound of the present invention through in vivo assay with use of animal models with a pancreatic cancer cell (MIA PaCa-2 cell) line transplanted. (A): A graph representing temporal variation of the surface area (mm²) of transplanted cancer cells. (B): A graph representing the mass (mg) of cancer cells on Day 28 after transplantation. *: p<0.05 (vs control, Student's t-test)

FIG. 2-2 shows graphs representing results of evaluation on the anti-cancer activity of the compound of the present invention through in vivo assay with use of animal models with a colorectal cancer cell (SW620 cell) line transplanted. (A): A graph representing temporal variation of the surface area (mm²) of transplanted cancer cells. (B): A graph representing the mass (mg) of cancer cells on Day 10 after transplantation. *: p<0.05 (vs control, Student's t-test)

FIG. 3 shows a graph representing results of evaluation on the cell death inducibility of the compound of the present invention for a colorectal cancer cell (SW620 cell) line through a TUNEL method. *: p<0.05 (vs control, Student's t-test)

DESCRIPTION OF EMBODIMENTS

1. Compound

Figure 1:
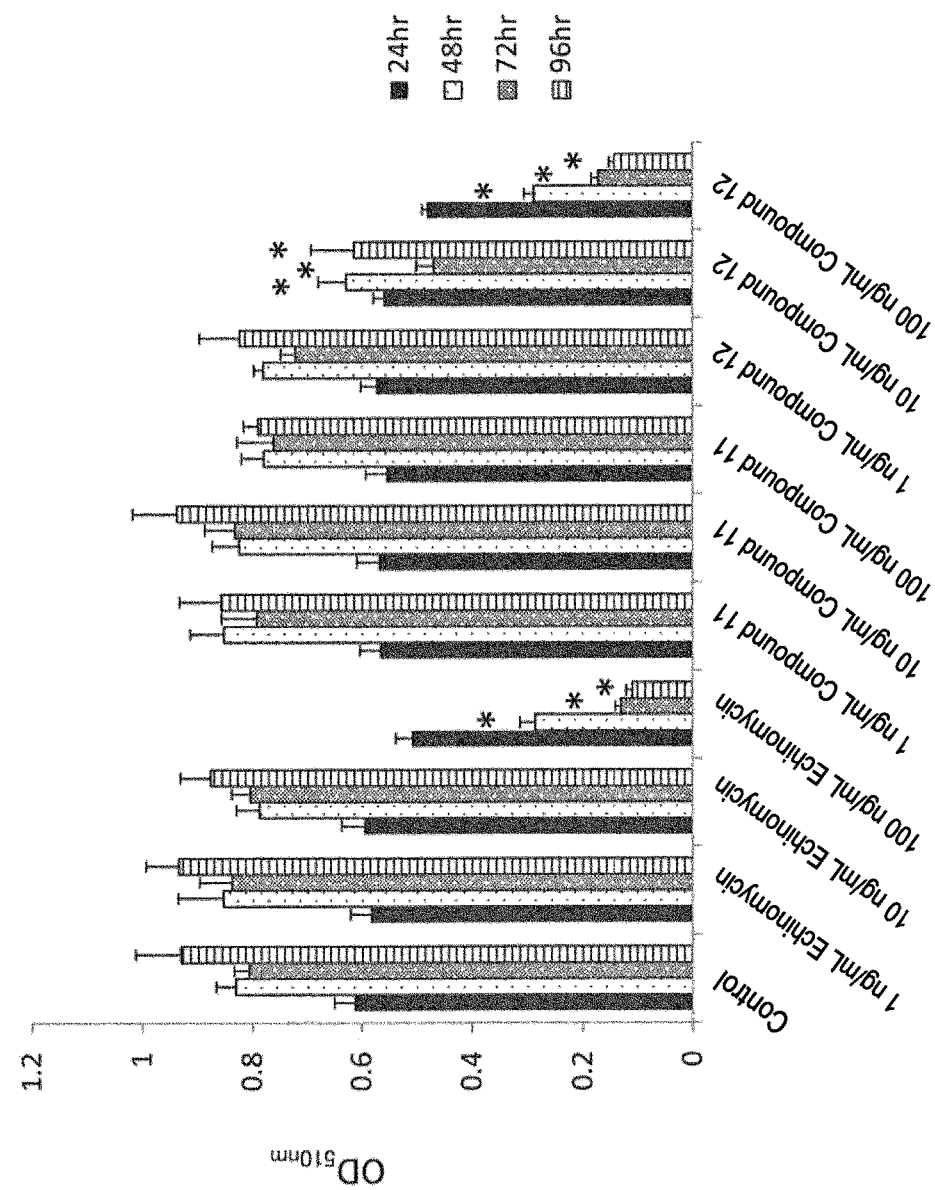
FIG. 1-1 shows a graph representing results of evaluation on the anti-cancer activity of the compound of the present invention through SRB assay with use of a pancreatic cancer cell (MIA PaCa-2 cell) line. *: $p<0.05$ (vs control, Student's t-test)

The compound of the present invention is represented by formula (I):

[Formula 11]

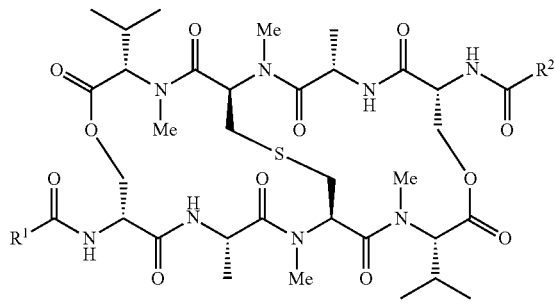

In the formula, $R^1$ and $R^2$ are each independently selectable and identical or different, and each represent an aromatic hydrocarbon group, saturated or unsaturated heterocyclic group, anthraquinone group, or benzophenone group optionally substituted with one or more substituents.

The term "substituent" refers to any of a hydrogen atom, a halogen atom, a hydroxy group, an amino group, a cyano group, a nitro group, an oxo group, an oxide group, an alkyl group, an alkenyl group, an alkynyl group, a haloalkyl group, an alkoxy group, a cycloalkyl group, the group —$OR^3$, the group —$SR^3$, the group —$NR^3R^4$, the group —$C(O)R^3$, the group —$C(O)NR^3R^4$, the group —$OC(O)NR^3R^4$, the group —$C(O)OR^3$, the group —$NR^3C(O)R^4$, the group —$NR^3C(O)OR^4$, the group —$NR^3C(O)NR^4R^5$, the group —$NR^3C(S)NR^4R^5$, the group —$NR^3S(O)_2R^4$, the group —$S(O)_2NR^3R^4$, the group —$S(O)R^3$ group, the group —$S(O)_2R^3$, and so on (here, $R^3$, $R^4$, and $R^5$ are each independently selectable and identical or different, and each represent any of a hydrogen atom, an alkyl group, a haloalkyl group, an alkenyl group, an alkynyl group, a cycloalkyl group, and so on).

The term "halogen atom" refers to, for example, a chlorine atom, a fluorine atom, a bromine atom, an iodine atom, and so on.

The term "alkyl group" refers to a linear or branched alkyl group, and examples thereof can include a methyl group, an ethyl group, a n-propyl group, an isopropyl group, a n-butyl group, an isobutyl group, a sec-butyl group, a tert-butyl group, a pentyl group, a hexyl group, and so on.

The term "alkenyl group" refers to a linear or branched alkenyl group including at least one carbon-carbon double bond, and examples thereof can include a vinyl group, an allyl group, a methylvinyl group, a propenyl group, a butenyl group, a pentenyl group, a hexenyl group, and so on.

The term "alkynyl group" refers to a linear or branched alkynyl group including at least one carbon-carbon triple bond, and examples thereof can include an ethynyl group, a 2-propynyl group, and so on.

The term "haloalkyl group" refers to a group in which one or more or all of the hydrogen atoms of an alkyl group are substituted with a halogen atom. Examples thereof can include a monofluoromethyl group, a difluoromethyl group, a trifluoromethyl group, a 1-fluoroethyl group, a 2-fluoroethyl group, a 1,1-difluoroethyl group, a 1,2-difluoroethyl group, a 2,2-difluoroethyl group, and so on.

The term "alkoxy group" refers to an oxy group to which an alkyl group is bonding, and examples thereof can include a methoxy group, an ethoxy group, a n-propoxy group, an isopropoxy group, a n-butoxy group, an isobutoxy group, a tert-butoxy group, and so on.

The term "cycloalkyl group" refers to a monocyclic or polycyclic alkyl group. Examples thereof can include a cyclopropyl group, a cyclobutyl group, a cyclopentyl group, a cyclohexyl group, a cycloheptyl group, a decalyl group, an adamantyl group, and so on.

The term "aromatic hydrocarbon group" refers to a monocyclic or polycyclic aromatic hydrocarbon group, which may be a group in which only some of the rings exhibit aromaticity. Examples of such aromatic hydrocarbon groups can include a phenyl group, a naphthyl group, a tetrahydronaphthyl group, and so on.

The term "saturated heterocyclic group" refers to a monocyclic or polycyclic saturated heterocyclic group including at least one heteroatom selected from the group consisting of nitrogen, oxygen, and sulfur. Examples of such saturated heterocyclic groups can include a pyrrolidinyl group, a piperidinyl group, a piperazinyl group, a hexamethyleneimino group, a morpholino group, a thiomorpholino group, a homopiperazinyl group, an oxetanyl group, a tetrahydrofuranyl group, a tetrahydropyranyl group, and so on.

The term "unsaturated heterocyclic group" refers to a monocyclic or polycyclic, completely unsaturated or partially unsaturated heterocyclic group including at least one heteroatom selected from the group consisting of nitrogen, oxygen, and sulfur. Examples of such unsaturated heterocyclic groups can include a quinolyl group, an isoquinolyl group, a quinazolinyl group, a quinoxalyl group, a cinnolyl group, an imidazolyl group, a thienyl group, a furyl group, a pyrrolyl group, an oxazolyl group, an isoxazolyl group, a triazolyl group, an isothiazolyl group, a thiadiazolyl group, a pyrazolyl group, a triazolyl group, a tetrazolyl group, a pyridyl group, a pyrazyl group, a pyrimidinyl group, a pyridazinyl group, an indolyl group, an isoindolyl group, an indazolyl group, a triazolopyridyl group, a benzimidazolyl group, a benzoxazolyl group, a benzothiazolyl group, a benzothienyl group, a benzofuranyl group, a benzothiophene group, a purinyl group, a methylenedioxyphenyl group, an ethylenedioxyphenyl group, a dihydrobenzofuranyl group, and so on.

Preferably, $R^1$ and $R^2$ in the compound of the present invention represented by formula (I) are each independently selectable and identical or different, and are each an unsaturated heterocyclic group, anthraquinone group, or benzophenone group optionally substituted with one or more substituents. For example, $R^1$ and $R^2$ in the compound of the present invention represented by formula (I) are each independently selectable and identical or different, and are each a quinolyl group, isoquinolyl group, quinazolinyl group, one or more substituents selected from the group consisting of a hydrogen atom, a halogen atom, a hydroxy group, and a $C_{1-6}$ alkyl group.

Specifically, $R^1$ and $R^2$ in the compound of the present invention represented by formula (I) are identical or different, and are each a 2-, 3-, 4-, 5-, 6-, or 7-indolyl group, 2-benzofuranyl group, 2- or 3-benzothiophene group, 5- or 6-benzoxazolyl group, 6-benzothiazolyl group, 6-pyrazyl group, 2-anthraquinone group, or 4-benzophenone group optionally substituted with one or more substituents selected from the group consisting of a hydrogen atom, a halogen atom, a hydroxy group, and a $C_{1-6}$ alkyl group.

Alternatively, $R^1$ and $R^2$ in the compound of the present invention represented by formula (I) are identical or different, and are each a 2-quinolyl group or a 2-quinolyl group having one substituent selected from a halogen atom, a hydroxy group, and a $C_{1-6}$ alkyl group at position 3, 4, 5, 6, 7, or 8; a 2-quinoxalyl group or a 2-quinoxalyl group having identical or different substituents each selected from the group consisting of a hydrogen atom, a halogen atom, a hydroxy group, and a $C_{1-6}$ alkyl group separately at two positions selected from positions 3, 4, 5, 6, 7, and 8. Preferably, $R^1$ and $R^2$ are each a 2-quinolyl group having said substituent at position 3 or a 2-quinoxalyl group having said substituent at each of positions 3 and 4.

Particularly preferably, the compound of the present invention is represented by formula (II):

[Formula 12]

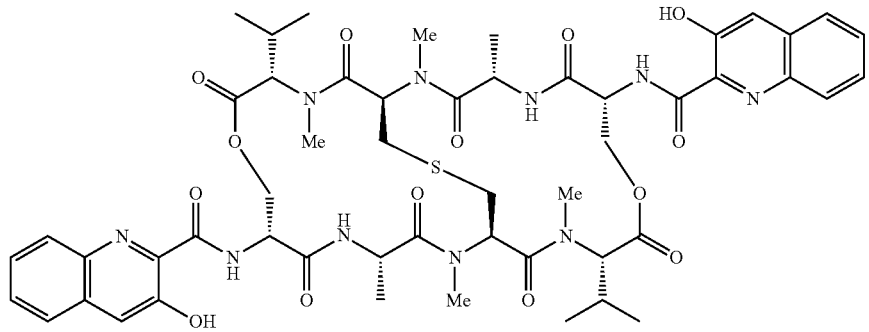

or formula (III):

[Formula 13]

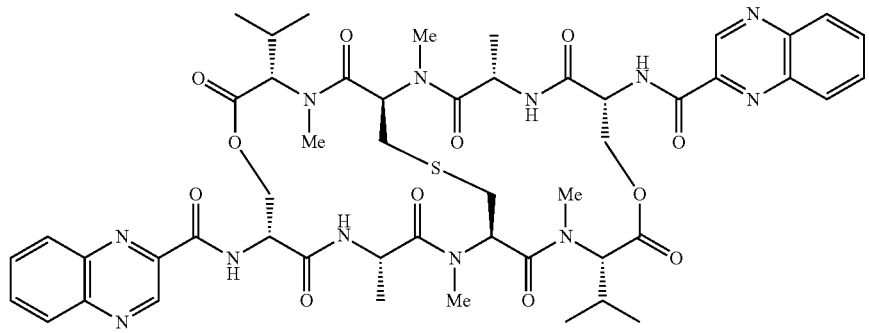

quinoxalyl group, cinnolyl group, indolyl group, benzofuranyl group, benzothiazolyl group, benzoxazolyl group, benzothiophene group, pyrazyl group, anthraquinone group, benzophenone group, and so on optionally substituted with If there exists an isomer of the compound of the present invention, such as an optical isomer, stereoisomer, regioisomer, rotamer, and tautomer, any isomer and mixtures of isomers are also included in the scope of the compound of the present invention. For example, if there exists an optical isomer of the compound of the present invention, an optical isomer obtained through optical resolution of a racemate is also included in the scope of the compound of the present invention.

The salt of the compound of the present invention may be any pharmaceutically acceptable salt, and the scope of the salt includes salts commonly used in the field of organic chemistry, examples of which include base addition salts and acid addition salts. Examples of base addition salts include alkali metal salts (e.g., sodium salts, potassium salts), alkali earth metal salts (e.g., calcium salts, magnesium salts), ammonium salts, and organic amine salts (e.g., trimethylamine salts, triethylamine salts, dicyclohexylamine salts, ethanolamine salts, diethanolamine salts, triethanolamine salts, procaine salts, N,N'-dibenzylethylenediamine salts). Examples of acid addition salts include inorganic acid salts (e.g., hydrochlorides, sulfates, nitrates, phosphates, perchlorates), organic acid salts (e.g., acetates, formates, maleates, fumarates, tartrates, citrates, ascorbates, trifluoroacetates), and sulfonates (e.g., methanesulfonates, isethionates, benzenesulfonates, p-toluenesulfonates).

The compound of the present invention or salt thereof may be in the form of a crystal. The crystal form may be a single crystal or a polymorphic mixture, which can be produced by using a conventionally known crystallization method. The compound of the present invention or salt thereof may be in the form of a solvate (e.g., a hydrate), or in the form of a non-solvate. The compound of the present invention or salt thereof may be labeled with an isotope (e.g., deuterium, $^3H$, $^{14}C$, $^{35}S$, $^{125}I$).

2. Production Method

The compound of the present invention represented by formula (I) can be produced, for example, by using a method described later or methods shown in Examples. However, the manner of producing the compound of the present invention represented by formula (I) is not limited to these reaction examples.

Examples of the "protective group for an amino group" in the production method for the compound described later include, but are not limited to, a Boc group, a benzyloxycarbonyl group, a 4-methoxybenzyl group, a 2,4,6-trimethoxybenzyl group, a 2,4-dimethoxybenzyl group, a 4-methoxybenzyl group, and so on.

Examples of the "protective group for a carboxy group" in the production method for the compound described later include, but are not limited to, an allyl group, an alkyl group, a cycloalkyl group, a t-butyl group, a benzyl group, a methoxybenzyl group, a nitrobenzyl group, a trichloroethyl group, a phenacyl group, and so on.

In the production method for the compound described later, "removal of a protective group (deprotection)" can be performed by using a known procedure. Applicable as the solvent are trifluoroacetic acid, methanesulfonic acid, trifluoromethanesulfonic acid, p-toluenesulfonic acid, hydrochloric acid, sulfuric acid, acetic acid, formic acid, triethylamine, diisopropylethylamine, pyridine, isopropanol, tert-butyl alcohol, toluene, benzene, methylene chloride, chloroform, tetrahydrofuran, dioxane, dimethylformamide, dimethylacetamide N-methylpyrrolidinone, dimethylsulfoxide, and so on, and an appropriate solvent can be selected according to the type of a protective group selected to be removed (and a protective group not to be removed). As necessary, anisole, phenol, thioanisole, meta-cresol, para-cresol, dimethylsulfide, 1,4-butanedithiol, 1,2-ethanedithiol, a Pd catalyst, or liquid ammonia can be added to the reaction. The reaction can be performed by reacting in a solvent at −78° C. to 200° C., preferably at 25° C. to 100° C., more preferably at 30° C. to 50° C. for 10 minutes to 24 hours, more preferably for 30 minutes to 12 hours.

In the production method for the compound described later, "condensation reaction" can be performed by using a known procedure, and can be performed by reacting in a solvent to which a condensation agent has been added at −78° C. to 200° C., preferably at 25° C. to 100° C., more preferably at 30° C. to 50° C., for 10 minutes to 3 days, preferably for 1 hour to 24 hours, more preferably for 3 to 15 hours.

Applicable as the condensation agent are, for example, 1-ethyl-3-(3-dimethylaminopropyl)carbodiimide, a combination of 1-ethyl-3-(3-dimethylaminopropyl)carbodiimide and 1-hydroxybenzotriazole, diphenylphosphoryl azide, N,N'-dicyclohexylcarbodiimide, benzotriazol-1-yloxy-tris-dimethylamino phosphonium salt, 4-(4,6-dimethoxy-1,3,5-triazin-2-yl)-4-methyl morpholinium chloride, 2-chloro-1,3-dimethylimidazolinium chloride, 0-(7-azabenzotriazo-1-yl)-N,N,N',N'-tetramethylhexauronium hexafluorophosphate, 3H-1,2,3-triazolo[4,5-b]pyridin-3-ol, and so on.

Applicable as the solvent for the condensation reaction are, for example, dimethylformamide, isopropanol, tert-butyl alcohol, toluene, benzene, methylene chloride, chloroform, tetrahydrofuran, dioxane, dimethylacetamide, N-methylpyrrolidinone, dimethylsulfoxide, and mixed solvents of them.

A base can be further added to the solvent in the condensation reaction. Applicable as the base are inorganic bases (e.g., sodium hydrogen carbonate, sodium carbonate, potassium carbonate, cesium carbonate, sodium hydroxide, sodium hydride), and organic bases (e.g., triethylamine, diisopropylethylamine, pyridine, lutidine, collidine, 4-dimethylaminopyridine, potassium-tert-butyrate, sodium-tert-butyrate, sodium methoxide, sodium ethoxide, lithium hexamethyldisilazide, sodium hexamethyldisilazide, potassium hexamethyldisilazide, butyllithium).

In the production method for the compound described later, a compound obtained in each step can be isolated/purified by using a separation means for compounds. Means commonly used for isolation/purification of compounds can be used as the "separation means for compounds", and examples thereof include solvent extraction, recrystallization, preparative reverse-phase high-performance liquid chromatography, column chromatography, and preparative thin-layer chromatography.

The compound of the present invention represented by formula (I) can be produced by using a method including step 1 to step 3 described in the following.

(Step 1)

This step is a step of producing a compound represented by formula (3) from a compound represented by formula (1) and a compound represented by formula (2):

[Formula 14]

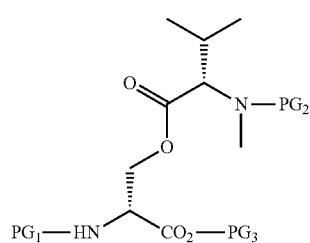

(Formula 1)

-continued

[Formula 15]

(Formula 2)

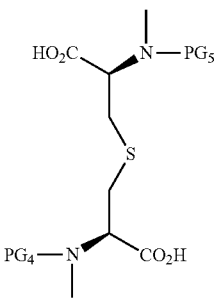

[Formula 16]

(Formula 3)

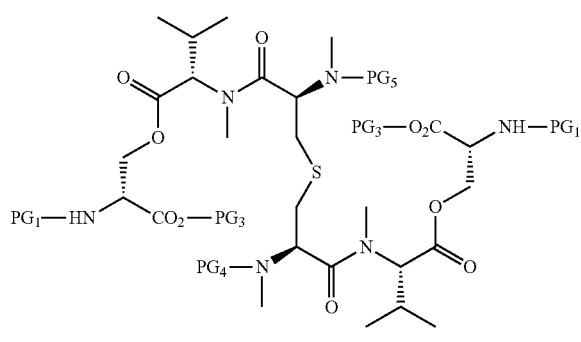

In the formulas, $PG_1$ represents a conventional protective group for an amino group, and is preferably a benzyloxycarbonyl group.

In the formulas, $PG_2$ represents a conventional protective group for an amino group, provided that $PG_2$ is different from $PG_1$, and is preferably a Boc group.

In the formulas, $PG_3$ represents a conventional protective group for a carboxy group, and $PG_3$ is preferably an allyl group.

In the formulas, $PG_4$ and $PG_5$ each represent a conventional protective group for an amino group, provided that $PG_4$ and $PG_5$ are different from $PG_1$, and $PG_4$ and $PG_5$ may be identical or different, but are preferably identical and each a Boc group.

In this step, the compound represented by formula (1) is subjected to deprotection reaction for the group represented as $PG_2$. Subsequently, the compound represented by formula (3) can be obtained through condensation reaction of the deprotected compound obtained and the compound represented by formula (2).

The compound represented by formula (1) as a raw material can be produced from a compound represented by formula (1a) and a compound represented by formula (1b) in accordance with a known procedure (Nagasawa, H. et al. Org. Biomol. Chem. 2016, 14, 2090):

[Formula 17]

(Formula 1a)

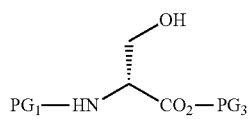

[Formula 18]

(Formula 1b)

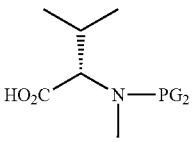

The compound represented by formula (2) as a raw material can be produced from a compound represented by formula (2a):

[Formula 19]

(Formula 2a)

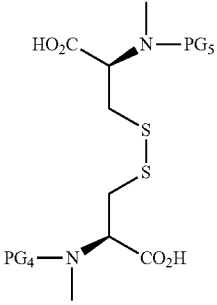

and can be obtained in such a procedure that the carboxy group of the compound represented by formula (2a) is protected, the compound is then treated with a trivalent phosphorous compound to remove one sulfur atom, and thereafter the protective group for the carboxy group is removed for deprotection. For the trivalent phosphorus compound, for example, tris(dimethylamino)phosphine can be used.

$PG_1$, $PG_2$, $PG_3$, $PG_4$, and $PG_5$ in formulas (1a), (1b), and (2a) are as defined above.

(Step 2)

This step is a step of reacting the above compound represented by formula (3) and a compound represented by formula (4) to produce a compound represented by formula (5) and then producing a compound represented by formula (6) from the compound represented by formula (5):

[Formula 20]

(Formula 4)

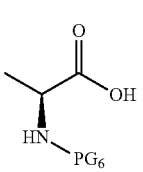

[Formula 21]

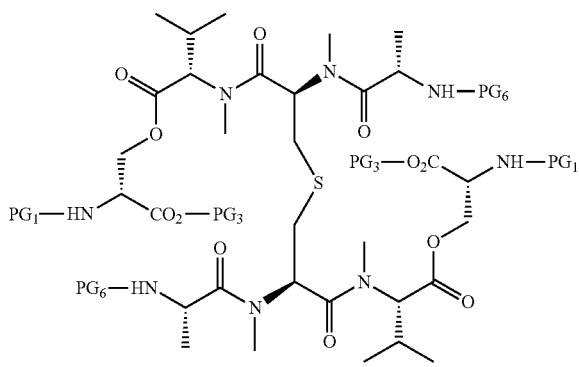

(Formula 5)

[Formula 22]

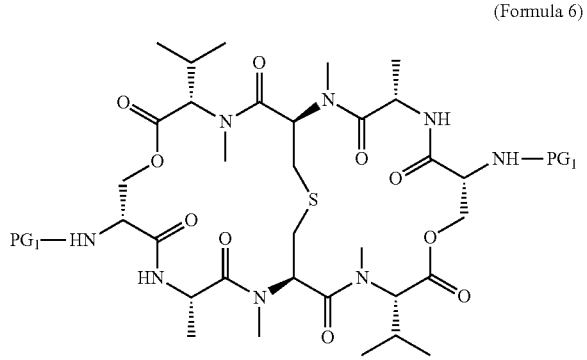

(Formula 6)

In the formulas, $PG_6$ represents a conventional protective group for an amino group, provided that $PG_6$ is different from $PG_1$, and is preferably a Boc group. Preferably, N-(tert-butoxycarbonyl)-L-alanine can be used as the compound represented by formula (4).

$PG_1$, $PG_3$, $PG_4$, and $PG_5$ are as defined above.

The compound represented by formula (3) is subjected to deprotection reaction for the groups represented as $PG_4$ and $PG_3$. The compound represented by formula (5) can be obtained through condensation reaction of the deprotected compound obtained and the compound represented by formula (4).

Subsequently, the compound represented by formula (5) is subjected to deprotection reaction for the groups represented as $PG_3$ and $PG_6$. The compound represented by formula (6) can be obtained by subjecting the deprotected compound obtained to condensation reaction.

(Step 3)

This step is a step of producing the intended compound represented by formula (I) from the compound represented by formula (6) and compounds represented by formula (7):

[Formula 23]

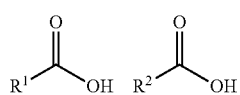

(Formula 7)

In the formula, $R^1$ and $R^2$ are synonymous with $R^1$ and $R^2$ in the above. If $R^1$ and $R^2$ are identical, these are the same compound.

In this step, the compound represented by formula (6) is subjected to deprotection reaction for the group represented as $PG_1$. The intended compound represented by formula (I) can be obtained through condensation reaction of the deprotected compound obtained and the compounds represented by formula (7).

3. Uses

The compound of the present invention or salt thereof can be used as an active ingredient of a pharmaceutical composition for treating cancer (referred to as "the pharmaceutical composition of the present invention").

The term "cancer" in the present invention encompasses solid cancer and hematological cancer (e.g., leukemia, malignant lymphoma, multiple myeloma), but preferably refers to solid cancer. The scope of solid cancer includes all non-hematological solid cancers (i.e., epithelial cell cancers and non-epithelial cell cancers). Examples of such solid cancers include, but are not limited to, brain tumor/glioma, pituitary adenoma, acoustic neurinoma, uveal malignant melanoma, meningioma, nasopharyngeal cancer, laryngeal cancer, tongue cancer, thyroid cancer, breast cancer, lung cancer, thymoma, thymic cancer, mesothelioma, esophageal carcinoma, gastric cancer, colorectal cancer, hepatocellular carcinoma, bile duct cancer, pancreatic cancer, renal cell carcinoma, bladder cancer, prostate cancer, renal pelvis/ureteric cancer, penile cancer, testicular tumor, uterine cancer, ovarian cancer, vulvar carcinoma, skin cancer, malignant melanoma (skin), basal cell carcinoma, prodromal symptoms of skin cancer, intraepidermal carcinoma, spinocellular carcinoma, mycosis fungoides, malignant bone tumor (osteosarcoma), soft part sarcoma, chondrosarcoma, malignant fibrous histiocytoma, and metastatic cancers of them.

The term "treatment" in the present invention refers not only to achieving a state in which cancer has completely disappeared, but also to a state in which cancer has temporarily or permanently reduced or disappeared and a state in which cancer is stable without progression (exacerbation). For example, the scope of "treatment" of cancer in the present invention includes one or more of reduction in size of cancer, lowering of a cancer marker level, amelioration of symptoms associated with cancer, and prolongation of measures including overall survival, progression-free survival, median survival time, and so on, in a patient as compared with the state before administration or ingestion of the compound of the present invention or salt thereof.

In addition to the compound of the present invention or salt thereof, the pharmaceutical composition of the present invention can contain a diluent, a binder, a disintegrant, a lubricant, and so on, commonly used in production of drugs, and can be produced as a dosage form suitable for intended dosage and administration.

Examples of the diluent include saccharides (monosaccharides, disaccharides, and polysaccharides such as cyclodextrin and alginic acid), metal salts, kaolin, silicic acid, polyethylene glycol, and mixtures of them.

Examples of the binder include simple syrup, glucose solution, starch solution, gelatin solution, polyvinyl alcohol, polyvinyl ether, polyvinyl pyrrolidone, carboxymethylcellulose, shellac, methylcellulose, ethylcellulose, and mixtures of them.

Examples of the disintegrant include dry starch, sodium alginate, agar powder, laminaran powder, sodium hydrogen carbonate, calcium carbonate, polyoxyethylene sorbitan fatty acid ester, sodium laurylsulfate, stearic acid monoglyceride, starch, lactose, and mixtures of them.

Examples of the lubricant include purified talc, stearates, borax, polyethylene glycol, and mixtures of them.

As necessary, a diluting agent, a stabilizer, an isotonic agent, a pH-adjusting agent, a buffering agent, a dissolution aid, a suspending agent, a coloring substance, a taste-masking agent, an odor-masking agent, a coating agent, a preservative, an antiseptic agent, an antioxidant, and so on can be appropriately contained.

Examples of dosage forms suitable for oral administration include a tablet, a pill, a capsule, a granule, a powder, a syrup, and a suspension. Solid dosage forms can be coated, as necessary (e.g., a sugar-coated tablet, a gelatin-coated tablet, an enteric-coated tablet).

Examples of dosage forms suitable for parenteral administration include an injection and a drip infusion. Each of these dosage forms may be a dosage form that is provided in a state that allows storage as a freeze-dried product, dissolved in a buffer solution or the like containing water, physiological saline, or the like to an appropriate concentration at time of use for preparation, and then used. Alternatively, dosage forms of a suppository, an ointment, an inhalation, a patch, and so on may be used.

The compound of the present invention or salt thereof in the form of a prodrug may be contained in the pharmaceutical composition of the present invention. The term "prodrug" refers to a compound that is converted into the compound of the present invention or salt thereof through reaction, for example, caused by an enzyme or gastric acid under physiological conditions in a living body, that is, a compound that changes into the compound of the present invention or salt thereof, for example, through the occurrence of enzymatic oxidation, reduction, or hydrolysis, or a compound that changes into the compound of the present invention or salt thereof, for example, through the occurrence of hydrolysis, for example, caused by gastric acid. The prodrug of the compound of the present invention or salt thereof may be a compound that changes into the compound of the present invention or salt thereof under physiological conditions as described in "Pharmaceutical research and development", vol. 7 "Molecular Design", p. 163-198, Hirokawa Shoten Co., 1990.

The dose of the pharmaceutical composition of the present invention can vary depending on factors such as the type and seriousness of cancer in a patient, symptoms, body weight, age, sex, and so on of a patient, and cannot be determined in a general manner. However, an amount selected from approximately 0.05 to 5000 mg, preferably selected from 0.1 to 1000 mg, in terms of the amount of the compound of the present invention or salt thereof, can be administered to an adult (body weight: 50 kg) per day, with one administration or about two or three administrations in a day.

Hereinafter, the present invention will be more specifically described with reference to Examples. However, the present invention is by no means limited to them.

EXAMPLES

Example 1: Synthesis of Compounds (Nuclear Magnetic Resonance)
Nuclear magnetic resonance (hereinafter, $^1$H-NMR) spectra were measured by using a JEOL JMM-ECS-400, JEOL JNM-ECX-400P, and JEOL JNM-ECA-500 (JEOL Ltd.).

Chemical shifts in $^1$H-NMR were represented as δ values in ppm as tetramethylsilane was used as an internal standard, and spin coupling constants (J values) were represented in Hz.

Multiplicity of a signal was represented as the following abbreviations. s: singlet, d: doublet, t: triplet, q: quartet, m: multiplet, br: broad.

(Room Temperature)
Room temperature refers to a range of about 20° C. to 25° C., and non-aqueous reactions were performed under an argon atmosphere, unless otherwise stated.

(Mass Spectrometry)
Mass spectrometry was performed through an ESI (Electron Spray Ionization) method using an SQ Detector2 (Nihon Waters K.K.).

(Reaction Solvent)
Methylene chloride, N,N-dimethylformamide, and benzene were distilled with diphosphorus pentoxide, calcium hydride, and metal sodium, respectively, and used as reaction solvents. Deionized water was purified with the ultrapure water production apparatus Millipore Millia-Q (R) Advantage A10 (R), and used as water. For other reagents and solvents, commercially available products were used, unless otherwise stated.

(Chromatography)
Merck silica gel 60 $F_{254}$ was used for analytical thin-layer chromatography (TLC). Wakogel 60N (63 to 212 μm) was used as a packing material for silica gel column chromatography, Kanto Chemical Silica Gel 60N (spherical, neutral, 40 to 50 μm) was used as a packing material for flash silica gel column chromatography, and CHROMATOREX PSQ60B was used as a packing material for high-flash silica gel column chromatography. Scavenger SH Silica from FUJI SILYSIA CHEMICAL LTD. was used as SH silica gel for removal of heavy metals.

Synthesis of the compound of the present invention was performed as follows.

Synthesis of Compound 1

Compound 1 (19.5 g, 69.8 mmol, 73%, two steps) was obtained as a colorless oily substance from D-Ser (10.0 g, 95.2 mmol) as a starting material under the same conditions as in a known procedure (Kohn, H. et al. J. Med. Chem. 2011, 54, 4815. Kunz, H.; Friedrich-Bochnitschek, S. J. Org. Chem. 1989, 54, 751.)

[Formula 24]

Compound 1

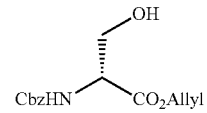

$^1$HNMR (CDCl$_3$, 400 MHz) δ 7.34-7.29 (m, 5H, Ar), 5.93-5.84 (m, 1H, CH═CH$_2$), 5.80 (d, 1H, Ser-NH, $J_{Ser-NH, Ser-\alpha-CH}$ = 6.8 Hz), 5.33 (d, 1H, CH═CH$_2$), $J_{trans}$ = 17.6 Hz), 5.25 (d 1H, CH═CH$_2$), $J_{cis}$ = 10.5 Hz), 5.12 (s 2H, Bn), 4.66 (d, 2H, Allyl, J = 5.0 Hz), 4.46 (dd, 1H, Ser-α-CH, $J_{ser-\alpha-CH, Ser-\beta-CH}$ = 4.7, $J_{Ser-\alpha-CH, Ser-\beta'-CH}$ = 3.7 Hz), 3.99 (dd, 1H, Ser-β-CH, $J_{gem}$ = 11.2, $J_{Ser-\beta-CH, Ser-\alpha-CH}$ = 3.7 Hz), 3.91 (dd, 2H, Ser-β-CH, $J_{gem}$ = 11.2, $J_{Ser-\beta-CH, Ser-\alpha-CH}$ = 4.7 Hz), 2.56 (d, 1H, Ser-OH, $J_{Ser-CH, Ser-\beta-CH}$ = 5.5 Hz) ESIMS-LR, m/z 302.24 [(M + Na)$^+$]

Synthesis of Compound 2

Compound 2 (15.1 g, 65.3 mmol, 95%) was obtained as a pale-yellow oily substance from Boc-L-Val-OH (15.0 g, 69.0 mmol) as a starting material under the same conditions as in a known procedure (Nagasawa, H. et al., shown above).

[Formula 25]

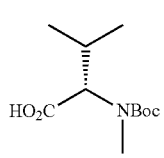

Compound 2

$^1$HNMR (CDCl$_3$, 400 MHz, selected data for a rotamer) δ 3.99 (d, 1H, Val-α-CH, J$_{Val-α-CH, Val-β-CH}$ = 11.0 Hz), 2.88 (s, 3H, Val-N-CH), 2.37 - 2.31 (m, 1H, Val-β-CH), 1.47 (s, 9H, Boc), 1.02 (d, 6H, Val-γ-CH, J$_{Val-γ-CH, Val-β-CH}$ = 6.9 Hz), 0.92 (d, 6H, Val-γ-CH, J$_{Val-γ-CH, Val-β-CH}$ = 6.9 Hz)
ESIMS-LR, m/z 254.17 [(M + Na)$^+$]

Synthesis of Compound 3

Compound 3 (6.48 g, 13.2 mmol, 64%) was obtained as a colorless oily substance from compound 1 (5.78 g, 20.7 mmol) and compound 2 (4.79 g, 20.7 mmol) under the same conditions as in a known procedure (Nagasawa, H. et al., shown above).

[Formula 26]

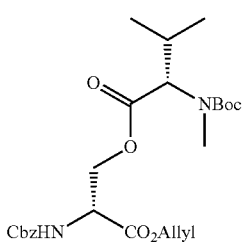

Compound 3

$^1$HNMR (DMSO-d6, 400 MHz, selected data for a rotamer) δ 7.90 (d, 1H, Ser-NH, J$_{Ser-NH, Ser-α-CH}$ = 8.2 Hz), 7.39-7.32 (m, 5H, Ar), 5.87 (ddt, 1H, CH═CH$_2$, J$_{trans}$ = 17.4, J$_{cis}$ = 11.0, J = 5.5 Hz), 5.31 (d, 1H, CH═CH$_2$, J$_{trans}$ = 17.4 Hz), 5.22 (d, 1H CH═CH$_2$, J$_{cis}$ = 11.0 Hz), 5.05 (s, 2H, Bn), 4.60 (d, 2H, Allyl, J = 5.5 Hz), 4.49 (br, s, 1H, Ser-α-CH), 4.32-4.27 (m, 2H, Ser-β-CH), 4.01 (d, 1H, Val-α-CH, J$_{Val-α-CH, Val-β-CH}$ = 10.1 Hz), 2.72 (s, 3H, Val-N-CH), 2.12 (br, s, 1H, Val-β-CH), 1.38 (s, 9H, Boc), 0.88 (d, 6H-Val-γ-CH, J$_{Val-γ-CH, Val-β-CH}$ = 6.4 Hz), 0.79 (d, 6H, Val-γ-CH, J$_{Val-γ-CH, Val-β-CH}$ = 6.4 Hz)
ESIMS-LR m/z 493.42 [(M + H)$^+$]

Synthesis of Compound 4

Compound 4 (24.6 g, 52.5 mmol, 28%, three steps) was obtained as a white foamy substance from (R)-thiazolidinecarboxylic acid (50.0 g, 375 mmol) as a starting material under the same conditions as in a known procedure (US20140187546).

[Formula 27]

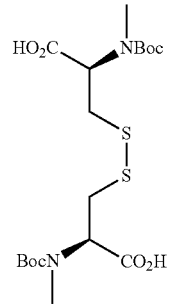

Compound 4

$^1$HNMR (CDCl$_3$, 400 MHz) δ 4.88-4.72 (M, 2H, Cys-α-CH), 3.32 (dd, 2H, Cys-β-CH, J$_{gem}$ = 14.2 J$_{Cys-β-CH, Cys-α-CH}$ = 4.6 Hz), 3.00-2.92 (m, 8H, Cys-β-H, Cys-N-CH), 1.47-1.43 (m, 18H, Boc)
ESIMS-LR m/z 469.21 [(M + H)$^+$]

Synthesis of Compound 5

Methyl iodide (7.41 mL, 119 mmol) was added to a suspension of compound 4 (25.4 g, 54.2 mmol) and potassium carbonate (16.4 g, 119 mmol) in dimethylformamide (180 mL) under ice-cooling, and the resultant was stirred for 1.5 hours. Methyl iodide (0.74 mL, 11.9 mmol) was further added thereto, and the resultant was stirred for 1.5 hours. The reaction solution was diluted with ethyl acetate, washed sequentially with water, saturated aqueous solution of sodium thiosulfate, and brine, and then dried over anhydrous sodium sulfate. The solvent was distilled off under reduced pressure, and the resulting residue was dissolved in benzene (42 mL), to which trisdimethylaminophosphine (11.8 mL, 65.0 mmol) was added, and the resultant was stirred at room temperature for 24 hours. The solvent of the reaction solution was distilled under reduced pressure, and the resulting residue was purified by flash silica gel column chromatography (φ6.5×25 cm, hexane/ethyl acetate: 11/3→11/7) to afford compound 5 (22.7 g, 48.8 mmol, 90%, two steps) as a pale-yellow oily substance.

[Formula 28]

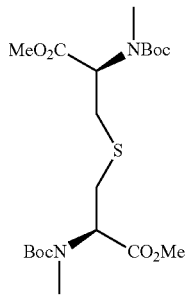

Compound 5

$^1$HNMR (CDCl$_3$, 400 MHz, selected data for a rotamer) δ 4.74 (dd, 2H, Cys-α-CH, J$_{Cys-α-CH, Cys-β-CH}$ = 10.7, 5.3 Hz), 3.73 (s, 6H, CO$_2$CH$_3$), 3.13 (dd, 2H, Cys-β-CH, J$_{gem}$ = 10.5, J$_{Cys-β-CH, Cys-α-CH}$ = 5.3 Hz), 3.00-2.28 (m, 8H, Cys-β-CH, Cys-N-CH), 1.46 (s, 18H, Boc)
ESIMS-LR m/z 465.24 [(M + H)$^+$]

Synthesis of Compound 6

A solution of lithium hydroxide hydrate (4.74 g, 113 mmol) in water (100 mL) was added to compound 5 (23.9 g, 51.4 mmol) in a mixed solvent of tetrahydrofuran (150 mL), methanol (50 mL), and water (50 mL) under ice-cooling, and the resultant was stirred for 1 hour. A solution of lithium hydroxide hydrate (474 mg, 11.3 mmol) in water (10 mL) was added thereto under ice-cooling, and the resultant was stirred for 30 minutes. The solvent of the reaction solution was distilled off under reduced pressure to concentrate to about 150 mL, and 1 M aqueous solution of hydrochloric acid was added to the resulting residue, which was extracted with chloroform. The extract was washed with brine, and dried over anhydrous sodium sulfate. The solvent was distilled off under reduced pressure to afford compound 6 (22.4 g, 51.3 mmol, quantitative yield) as a white foamy substance.

[Formula 29]

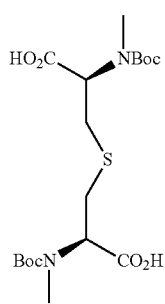

Compound 6

$^1$HNMR (DMSO-d6, 400 MHz) d 4.66-4.31 (m, 2H, Cys-α-CH), 3.10-2.81 (m, Cys-β-CH), 2.76-2.71 (m, 6H, Cys-N-CH), 1.44-1.36 (m, 18H, Boc)
ESIMS-LR m/z 437.21 [(M + H)$^+$]

Synthesis of Compound 7

To compound 3 (25.4 g, 69.0 mmol), 4 M hydrogen chloride/dioxane solution (100 mL, 400 mmol) was added, and the resultant was stirred at room temperature for 1 hour. The solvent was distilled off under reduced pressure, dioxane was added to the resulting residue, and the solvent was distilled off under reduced pressure to afford a white solid. To a suspension of the white solid, compound 6 (16.0 g, 34.5 mmol), and HOAt (12.2 g, 89.7 mmol) in methylene chloride (130 mL), diisopropylethylamine (17.0 mL, 100 mmol) and EDCI (17.2 g, 89.7 mmol) were added under ice-cooling, and the resultant was stirred at room temperature for 19 hours. The reaction solution was diluted with ethyl acetate, washed sequentially with 1 M aqueous solution of hydrochloric acid, saturated baking soda water, and brine, and then dried over anhydrous sodium sulfate. The solvent was distilled off under reduced pressure, and the resulting residue was purified by flash silica gel column chromatography (φ6.5×15 cm, hexane/ethyl acetate: 5/3→5/6) to afford compound 7 (30.6 g, 25.8 mmol, 74%, two steps) as a white foamy substance.

[Formula 30]

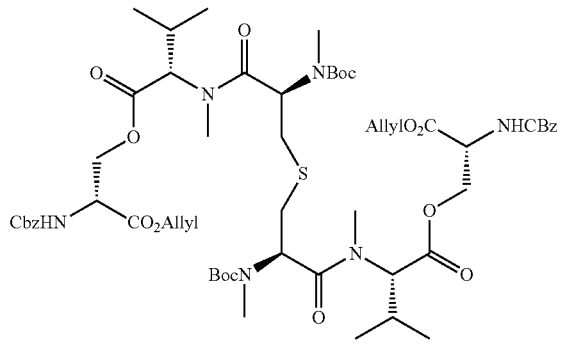

Compound 7

$^1$HNMR (DMSO-d$_6$, 400 MHz) δ 7.94-7.80 (m, 2H, Ser-NH), 7.38-7.31 (m, 10H, Ar), 5.88 (ddt, 1H, CH=CH$_2$, J$_{trans}$ = 17.4, J$_{cis}$ = 10.5, J = 5.2 Hz), 5.31 (d, 2H, CH=CH$_2$, J$_{trans}$ = 17.4, Hz), 5.21 (d, 2H, CH=CH$_2$, J$_{cis}$ = 10.5, Hz), 5.05 (s, 4H, Bn), 5.05 - 4.82 (m, 2H, Cys-α-CH), 4.71-3.95 (m, 12H, Allyl, Val-α-CH, Ser-α-CH, Ser-β-CH), 2.96-2.45 (m, 16h, Cys-β-CH, Val-N-CH, Cys-N-CH), 1.40 (s, 18H, Boc), 0.94-0.69 (m, 12H, Val-γ-CH)
ESIMS-LR m/z 1185.90 [(M + H)$^+$]

Synthesis of Compound 8

To a solution of compound 7 (21.1 g, 17.8 mmol) in methylene chloride (20 mL), 4 M hydrogen chloride/dioxane solution (50 mL) was added, and the resultant was stirred at room temperature for 1 hour. The solvent was distilled off under reduced pressure, dioxane was added to the resulting residue, and the solvent was distilled off under reduced pressure to afford a white solid. To a suspension of the white solid, Boc-Ala-OH (10.1 g, 53.4 mmol), and HOAt (9.69 g, 71.2 mmol) in dimethylformamide (23 mL) and methylene chloride (117 mL), sodium hydrogen carbonate (7.78 g, 92.6 mmol) was added at room temperature, and EDCI (13.6 g, 71.2 mmol) was added thereto under ice-cooling, and the resultant was stirred at room temperature for 14 hours. The reaction solution was diluted with ethyl acetate, washed sequentially with 1 M aqueous solution of hydrochloric acid, saturated baking soda water, and brine, and then dried over anhydrous sodium sulfate. The solvent was distilled off under reduced pressure, and the resulting residue was purified by flash silica gel column chromatography (φ4×15 cm, hexane/ethyl acetate: 3/1→1/1) to afford compound 8 (16.5 g, 12.5 mmol, 70%, two steps) as a white foamy substance.

[Formula 31]

Compound 8

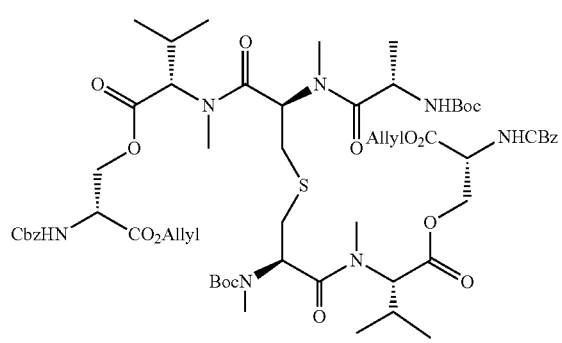

¹HNMR (DMSO-d₆, 500 MHz) δ 7.95-7.80 (m, 2H, Ser-NH),
7.35 - 7.31 (m, 10H, Ar), 7.08-6.85 (m, 2H, Ala-NH),
5.89 (ddt, 1H, CH=CH₂, J$_{trans}$ = 16.9, J$_{cis}$ = 11.0, J = 5.5 Hz),
5.53 - 5.38 (m, 2H, Cys-a-CH), 5.31 (d, 1H, CH=CH₂,
J$_{trans}$ = 16.9, Hz), 5.21 (d, 1H, CH=CH₂, J$_{cis}$ = 11.0, Hz), 5.05
(m, 4H, Bn), 4.59 (m, 4H, Allyl), 4.54-4.17 (m, 10H,
Val-α-CH, Ser-α-CH, Ala-α-CH Ser-β-CH), 2.96 - 2.45 (m, 16h,
Cys-β-CH, Val-N-CH, Cys-N-CH), 3.00-2.91 (m, 2H, Cys-β-CH),
2.84-2.40 (m, 14H, Cys-N-CH, Val-H-CH, Cys-b-CH)), 2.16
(m, 2H, Val-b-CH), 1.36 (s, 18H, Boc) 1.19 - 1.06 (m, 6H, Ala-β-CH)
ESIMS-LR m/z 1185.90 [(M + H)⁺]

[Formula 32]

Compound 9

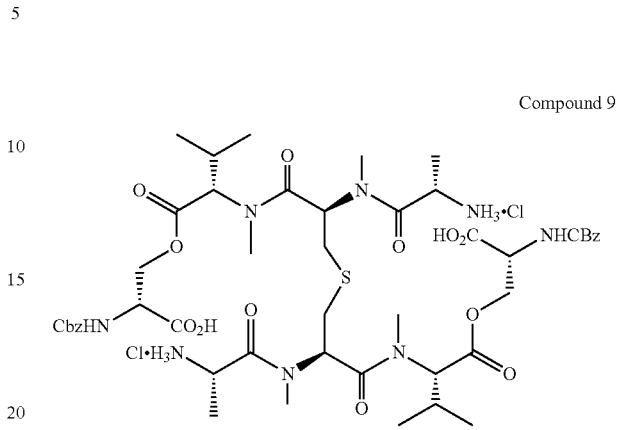

¹HNMR (DMSO-d₆, 400 MHz) δ 8.50 (br, s, 6H, Ala-NH), 7.81-7.70 (m,
2H, Ser-NH), 7.35 (m, 10H, Ar), 5.51-5.31 (m, 2H, Cys-α-CH), 5.03 (s, 4H,
Bn), 4.66-4.11 (m, 10H, Val-α-CH, Ser-α-CH,
Ala-α-CH, Ser-β-CH), 3.6-2.60 (m-16H, Cys-b-CH, Cys-N-CH,
Val-N-CH), 2.18 (m, 2H, Val-β-CH), 1.33-1.21 (m, 6H, Ala-β-CH), 0.98-
0.71 (m, 12H, Val-γ-CH)
ESIMS-LR m/z 1047.76 [(M + H)⁺]

Synthesis of Compound 9

Morpholine (5.12 mL, 58.8 mmol) and tetrakis(triphenylphosphine)palladium (38.9 mg, 33.6 μmol) were added to a solution of compound 8 (22.3 g, 16.8 mmol) in tetrahydrofuran (110 mL) under ice-cooling, and the resultant was stirred for 4 hours. The reaction solution was diluted with ethyl acetate, washed with 1 M aqueous solution of hydrochloric acid and brine, and then dried over anhydrous sodium sulfate. The solvent was distilled off under reduced pressure, and the resulting residue was partially purified by silica gel column chromatography including SH silica gel for removal of heavy metals on the top (φ4×2 cm, chloroform/methanol/acetic acid: 100/0/0→98/0/2→95/3/2) to afford a pale-yellow foamy compound. To this residue, 4 M hydrogen chloride/dioxane solution (100 mL) was added, and the resultant was stirred at room temperature for 1 hour. The solvent was distilled off under reduced pressure, dioxane was added to the resulting residue for solvent displacement, and then washed with diethyl ether to afford compound 9 (17.9 g, 16.0 mmol, 95%, two steps).

Synthesis of Compound 10

Diphenylphosphoryl azide (5.16 mL, 24.0 mmol) and N-methylmorpholine (3.69 mL, 33.6 mmol) were added to a solution of compound 9 (2.69 g, 2.40 mmol) in dimethylformamide (1.2 L) under ice-cooling, and the resultant was stirred at room temperature for 72 hours. The solvent of the reaction solution was distilled off under reduced pressure to concentrate to about 10 mL. This residue was diluted with ethyl acetate/mixed solvent, washed sequentially with water, 1 M aqueous solution of hydrochloric acid, saturated baking soda water, and brine, and then dried over anhydrous sodium sulfate. The solvent was distilled off under reduced pressure, and the resulting residue was purified by silica gel column chromatography (φ3×15 cm, chloroform/methanol: 100/0→99.5/0.5→99/1→98.5/1.5→98/2) to afford compound 10 (676 mg, 0.669 mmol, 28%) as a white solid.

[Formula 33]

Compound 10

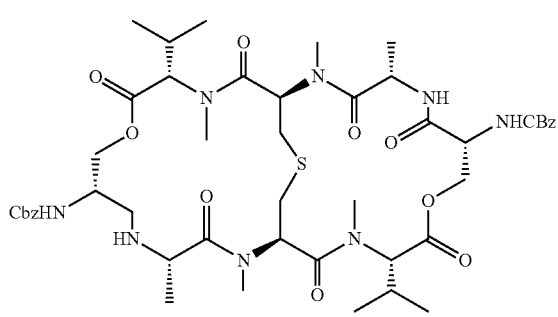

¹HNMR (DMSO-d₆, 400 MHz) δ 7.62 (d, 2H, Ala-NH, $J_{Ala\text{-}NH, Ala\text{-}\alpha\text{-}CH}$ = 5.2 Hz), 7.56 (d, 2H, Ser-NH, $J_{Ser\text{-}NH, Ser\text{-}\alpha\text{-}CH}$ = 5.2 Hz), 7.39-7.33 (m, 10H, Ar), 6.22 (t, 2H, Cys-α-CH, $J_{Cys\text{-}\alpha\text{-}CH, Cys\text{-}\beta\text{-}CH}$ = 6.6 Hz), 5.12 (d, 2H, Bn, $J_{gem}$ = 12.6 Hz), 5.06 (d, 2H, Bn, $J_{gem}$ = 12.6 Hz), 4.68 (d, 2H, Val-α-CH, $J_{Val\text{-}\alpha\text{-}CH, Val\text{-}\beta\text{-}CH}$ = 10.9 Hz), 4.53 (qd, 2H, Ala-α-CH, $J_{Aha\text{-}\alpha\text{-}CH, Ala\text{-}\beta\text{-}CH}$ = 6.3, $J_{Ala\text{-}\alpha\text{-}CH, Ala\text{-}NH}$ = 5.2 Hz), 4.24-4.21 (m, 6H, Ser-α-CH, Ser-β-CH), 3.01 (overlap, 2H, Cys-b-CH), 3.01, 2.76 (s, each 3H, Cys-N-CH, Val-b-CH), 2.38 (m, 2H, Cys-β-CH), 2.24 (m, 2H, Val-β-CH), 1.23 (d, 6H, Ala-b-CH, $J_{Ala\text{-}\beta\text{-}CH, Ala\text{-}\alpha\text{-}CH}$ = 6.3 Hz), 0.98 (d, 6H, Val-γ-CH, $J_{Val\text{-}\gamma\text{-}CH, Val\text{-}\beta\text{-}CH}$ = 6.3 Hz), 0.75 (d, 6H, Val-γ-CH, $J_{Val\text{-}\gamma\text{-}CH, Val\text{-}\beta\text{-}CH}$ = 6.9 Hz),
ESIMS-LR m/z 1011.87 [(M + H)⁺]

Synthesis of Compound 11

Trifluoroacetic acid (6.9 mL) was added to compound 10 (70.0 mg, 69.2 μmol) and methylphenyl sulfide (324 μL, 2.77 mmol), and the resultant was stirred at 40° C. for 15 hours. The reaction solution was concentrated under reduced pressure, and the resulting residue was washed with diethyl ether to afford a pale-yellow solid. This solid was added to a suspension of quinoxaline-2-carboxylic acid (48.2 mg, 0.277 mmol), HOAt (47.1 mg, 0.346 mmol), diisopropylethylamine (70.6 μL, 0.415 mmol), and EDCI (66.3 mg, 0.346 mmol) in dimethylformamide (1 mL) under ice-cooling, and the resultant was stirred at room temperature for 5 hours. The reaction solution was diluted with ethyl acetate, washed sequentially with water, 1 M aqueous solution of hydrochloric acid, saturated baking soda water, and brine, and then dried over anhydrous sodium sulfate. The solvent was distilled off under reduced pressure, and the resulting residue was purified by flash silica gel column chromatography (φ1×15 cm, chloroform/methanol: 100/0→99/1→98/2→97/3) to afford compound 11 (30.0 mg, 28.4 μmol, 41%, two steps) as a colorless solid.

[Formula 34]

Compound 11

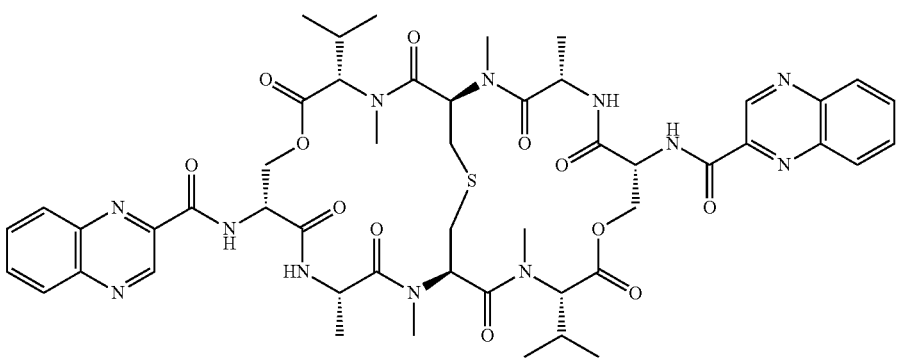

¹HNMR (CDCl₃, 400 MHz) δ 9.61 (s, 2H, Ar), 8.69 (d, 2H, Ser-NH, $J_{Ser\text{-}NH, Ser\text{-}\alpha\text{-}CH}$ = 7.4 Hz), 8.19-8.17 (m, 2H, Ar), 7.86-7.82 (m, 4H, Ar), 7.78-7.74 (m, 2H, Ar), 6.88 (d, 2H, Ala-NH, $J_{Ala\text{-}NH, Ala\text{-}\alpha\text{-}CH}$ = 7.3 Hz), 6.28 (dd, 2H, Cys-α-CH, $J_{Cys\text{-}\alpha\text{-}CH, Cys\text{-}\beta\text{-}CH}$ = 6.9, $J_{Cys\text{-}\alpha\text{-}CH, Cys\text{-}\beta'\text{-}CH}$ = 6.5 Hz), 5.15 (d, 2H, Val-α-CH, $J_{Val\text{-}\alpha\text{-}CH, Val\text{-}\beta\text{-}CH}$ = 10.6 Hz), 4.92-4.88 (m, 2H, Ser-α-CH), 4.84-4.79 (m, 4H, Ser-β-CH, Ala-α-CH), 4.68 (dd, 2H, Ser-β'-CH, $J_{gem}$ = 11.3, $J_{Ser\text{-}\beta'\text{-}CH, Ser\text{-}\alpha\text{-}CH}$ = 1.4 Hz), 3.39 (dd, 2H, Cys-β-CH, $J_{gem}$ = 15.1, $J_{Cys\text{-}\beta\text{-}CH, Cys\text{-}\alpha\text{-}CH}$ = 6.5 Hz), 3.17, 2.96 (s, each 6H, Cys-N-CH or Val-N-CH), 2.52 (dd, 2H, Cys-β'-CH, $J_{gem}$ = 15.1, $J_{Cys\text{-}\beta'\text{-}CH, Cys\text{-}\alpha\text{-}CH}$ = 6.9 Hz), 2.38-2.28 (m, 2H, Val-b-CH), 1.37 (d, 6H, Ala-b-CH, $J_{Ala\text{-}\beta\text{-}CH, Ala\text{-}\alpha\text{-}CH}$ = 6.9 Hz), 1.10 (d, 6H, Val-γ-CH, $J_{Val\text{-}\gamma\text{-}CH, Val\text{-}\beta\text{-}CH}$ = 6.9 Hz), 1.06 (d, 6H, Val-γ'-CH, $J_{Val\text{-}\gamma'\text{-}CH, Val\text{-}\beta\text{-}CH}$ = 6.9 Hz),
ESIMS-LR m/z 1055.93 [(M + H)⁺]

Synthesis of Compound 12

Trifluoroacetic acid (3.0 mL) was added to compound 10 (30.0 mg, 29.7 μmol) and methylphenyl sulfide (139 μL, 1.19 mmol), and the resultant was stirred at 40° C. for 15 hours. The reaction solution was concentrated under reduced pressure, and the resulting residue was washed with diethyl ether to afford a pale-yellow solid. This solid was added to a suspension of 3-hydroxyquinoline-2-carboxylic acid (16.9 mg, 89.1 μmol), HOAt (12.1 mg, 89.1 μmol), sodium hydrogen carbonate (20.0 mg, 238 μmol), and EDCI (17.1 mg, 89.1 μmol) in dimethylformamide (0.3 mL) under ice-cooling, and the resultant was stirred at room temperature for 5 hours. The reaction solution was diluted with ethyl acetate, washed sequentially with water, 1 M aqueous solution of hydrochloric acid, saturated baking soda water, and brine, and then dried over anhydrous sodium sulfate. The solvent was distilled off under reduced pressure, and the resulting residue was purified by flash silica gel column chromatography (ϕ1×15 cm, chloroform/methanol: 100/0→99/1→98/2→97/3) to afford compound 12 (9.6 mg, 8.8 μmol, 30%, two steps) as a colorless solid.

compound 12 was then added to the culture solution to reach a final concentration of 1 ng/mL, 10 ng/mL, 100 ng/mL, or 1000 ng/mL to initiate incubation, and the plate was taken out after 24 hours, 48 hours, 72 hours, and 96 hours (n=5 for each case).

To each well of the plate taken out, 100 μL of 10% trichloroacetic acid (TCA) was added, the plate was left to stand at 4° C. for 1 hour, and washed four times with pure water. The plate was dried at room temperature, 100 μL of 0.057% aqueous solution of sulforhodamine B was added to each well to stain cells, and the plate was washed four times with 0.1% acetic acid and then dried. Cell density after each incubation time was determined by measuring OD at 510 nm for stained cells lysed in 10 mM Tris buffer solution. No compound was added for a control group, and echinomycin was added for groups with administration of echinomycin so that the final concentration of echinomycin reached 1 ng/mL, 10 ng/mL, 100 ng/mL, or 1000 ng/mL, and the above-described operations were performed.

[Formula 35]

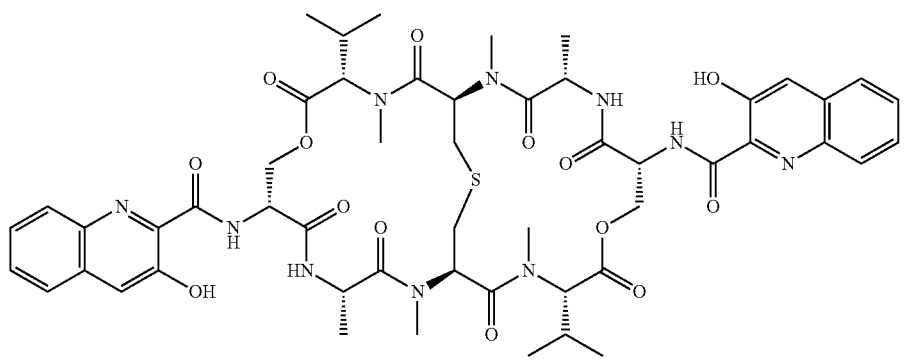

Compound 12

$^1$HNMR (CDCl$_3$, 400 MHz) δ 11.2 (s, 2H, Ar-OH), 9.10 (d, 2H, Ser-NH, J$_{Ser-NH, Ser-α-CH}$ = 6.9 Hz), 7.75-7.367 (m, 4H, Ar), 7.65 (S, 2H, Ar), 7.51-7.47 (m, 4H, Ar), 6.79 (d, 2H, Ala-NH, J$_{Ala-NH, Ala-α-CH}$ = 7.3 Hz), 6.28 (dd, 2H, Cys-α-CH, J$_{Cys-α-CH, Cys-β'-CH}$ = 7.3, J$_{Cys-α-CH, Cys-β-CH}$ = 6.9 Hz), 5.13 (d, 2H, Val-α-CH, J$_{Val-α-CH, Val-β-CH}$ = 10.5 Hz), 4.86 - 4.79 (m, 6H, Ser-α-CH), 4.68-4.64 (m, 4H, Ser-β'-CH), 3.38 (dd, 2H, Cys-β-CH, J$_{gem}$ = 15.1, J$_{Ser-β-CH, Ser-α-CH}$ = 6.9 Hz), 3.19, 3.25 (s, each 6H, Cys-N-CH or Val-N-CH), 2.51 (dd, 2H, Cys-β'-CH, J$_{gem}$ = 15.1, J$_{Cys-β'-CH, Cys-α-CH}$ = 7.3 Hz), 2.39-2.32 (m, 2H, Val-β-CH), 1.37 (d, 6H Ala-β-CH, J$_{Ala-β-CH, Ala-α-CH}$ = 7.3 Hz), 1.11 (d, 6H, Val-γ-CH, J$_{Val-γ-CH, Val-β-CH}$ = 6.4 Hz), 1.06 (d, 6H, Val-γ'-CH, J$_{Val-γ'-CH, Val-β-CH}$ = 6.9 Hz), ESIMS-LR m/z 1085.58 [(M + H)$^+$]

Example 2: Measurement of Anti-Cancer Activity (1) Experimental Method
(Cell Lines and Culture Thereof)

Used for cells were an SW620 cell line (ATCC), which was a colorectal cancer cell line, and an MIA PaCa-2 cell line (ATCC) and a Suit2 cell line (Health Science Research Resources Bank), which were a pancreatic cancer cell line.

Culture of the MIA PaCa-2 cell line and the Suit2 cell line was performed by using a DMEM with 10% FBS, 2 mM L-glutamine, 50 U/mL penicillin, and 50 μg/mL streptomycin. Culture of the SW620 cell line was performed by using RPMI1640 with 10% FBS, 2 mM L-glutamine, 50 U/mL penicillin, and 50 μg/mL streptomycin.

(SRB Assay)

Test cells aliquoted into a 96-well plate at 1.0×10$^4$ cells/well were cultured for 24 hours, and compound 11 or (Cell Death Inducibility)
1. TUNEL Method The SW620 cell line aliquoted into a 4-well glass chamber slide at 5.0×10$^4$ cells/well was cultured for 24 hours, and compound 12 was then added to the culture solution to reach a final concentration of 10 ng/mL to initiate incubation, and the slide was taken out after 48 hours.

By using a commercially available cell death detection kit utilizing a TUNEL (TdT-mediated dUTP nick-end labeling) method (In Situ Cell Death Detection Kit and TMR red (Roche Diagnostic)) in accordance with a protocol provided by the manufacturer, TUNEL-stained cells (i.e., cells that underwent cell death) were detected and counted. No compound was added for a control group, and echinomycin was added for a group with administration of echinomycin so that the final concentration of echinomycin reached 10 ng/mL, and the above-described operations were performed.

Each of the control group, group with administration of echinomycin, and group with administration of compound 12 was n=4.

2. Detection of Activated Caspase-3 (Western Blotting)

The SW620 cell line aliquoted into a 6-well plate at $2.0 \times 10^3$ cells/well was cultured for 24 hours, and compound 12 was then added to the culture solution to reach a final concentration of 10 ng/mL to initiate incubation, and the plate was taken out after 48 hours.

Proteins were collected by using a commercially available protein collection kit (mammalian cell extraction kit (Bio-Vision, Inc.)) in accordance with a protocol provided by the manufacturer, and activated caspase-3 was quantified through Western blotting with a specific antibody to cleaved caspase-3 (Cell Signaling Technology, Inc.). Actin was used as an endogenous control. No compound was added for a control group, and echinomycin was added for a group with administration of echinomycin so that the final concentration of echinomycin reached 10 ng/mL, and the above-described operations were performed.

Each of the control group, group with administration of echinomycin, and group with administration of compound 12 was n=4.

(Tumor-Cell-Transplanted Animal Model Assay 1—Evaluation on Size of Transplanted Tumor)

Anti-asialo GM1 (rabbit) (Wako Pure Chemical Industries, Ltd.) was intraperitoneally administered to BALB/c nude mice, and the mice were grown at room temperature for 2 hours. To the back of each BALB/c nude mouse, $2 \times 10^6$ test cells were subcutaneously injected for transplantation. Compound 11 or compound 12 in a dose of 50 ng or 500 ng or in a dose of 40 ng or 400 ng was intraperitoneally administered to each mouse on each day, from the day following the date of transplantation for mice with the SW620 cell line transplanted, from the day 1 week after the date of transplantation for mice with the MIA PaCa-2 cell line transplanted, and the growth of a tumor mass in each transplantation site was observed. No compound was administered to a control group, and echinomycin in a dose of 40 ng or 400 ng was intraperitoneally administered to each mouse in groups with administration of echinomycin on each day.

Each of the control group, groups with administration of echinomycin, groups with administration of compound 11, and groups with administration of compound 12 was n=5.

(Tumor-Cell-Transplanted Animal Model Assay 2—Evaluation on Body Weight Variation)

Anti-asialo GM1 (rabbit) (Wako Pure Chemical Industries, Ltd.) was intraperitoneally administered to BALB/c nude mice, and the mice were grown at room temperature for 2 hours. To the back of each BALB/c nude mouse, $2 \times 10^6$ cells of the MIA PaCa-2 cell line were subcutaneously injected for transplantation. Compound 11 or compound 12 in a dose of 500 ng was intraperitoneally administered to each mouse on each day from the day following the date of transplantation, and body weight was measured on each day (n=5 for each group). No compound was administered to a control group, and echinomycin in a dose of 400 ng was intraperitoneally administered to each mouse in a group with administration of echinomycin on each day, and body weight was measured at the date of slaughter (n=5 for each group).

(2) Results (SRB Assay)

Figures 1, 2:
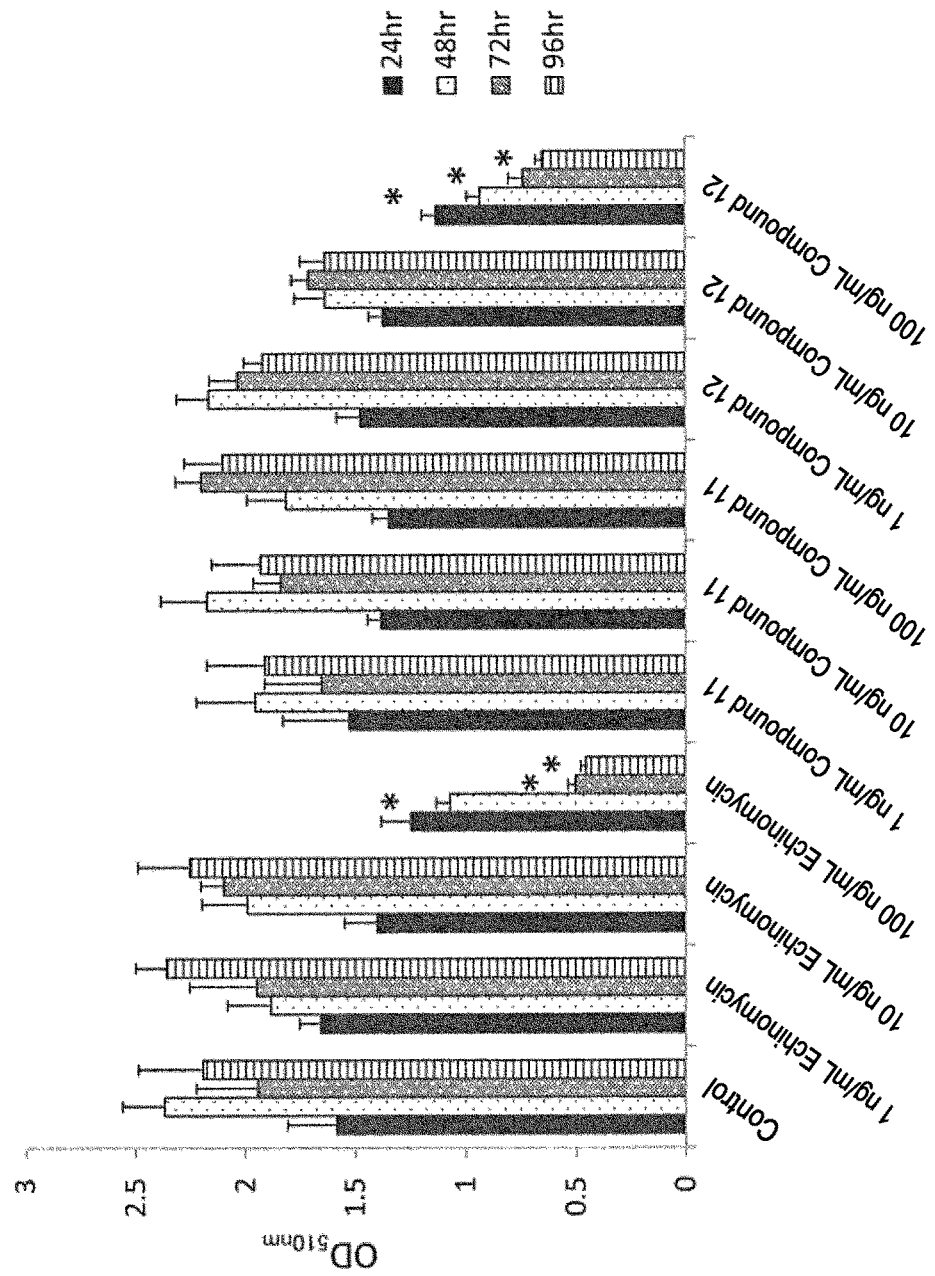
Figures 1, 2, 3:
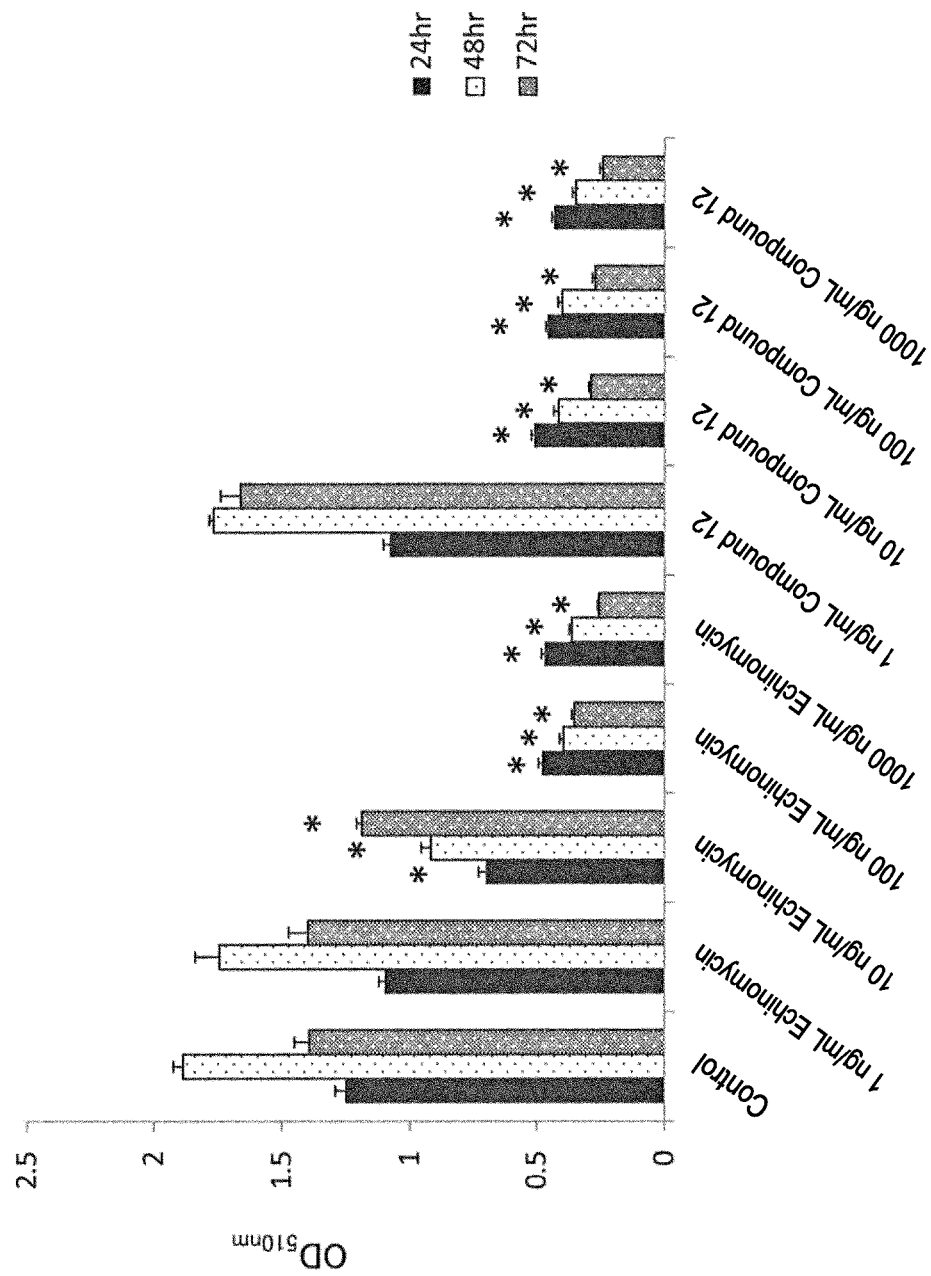
Figures 1, 2:
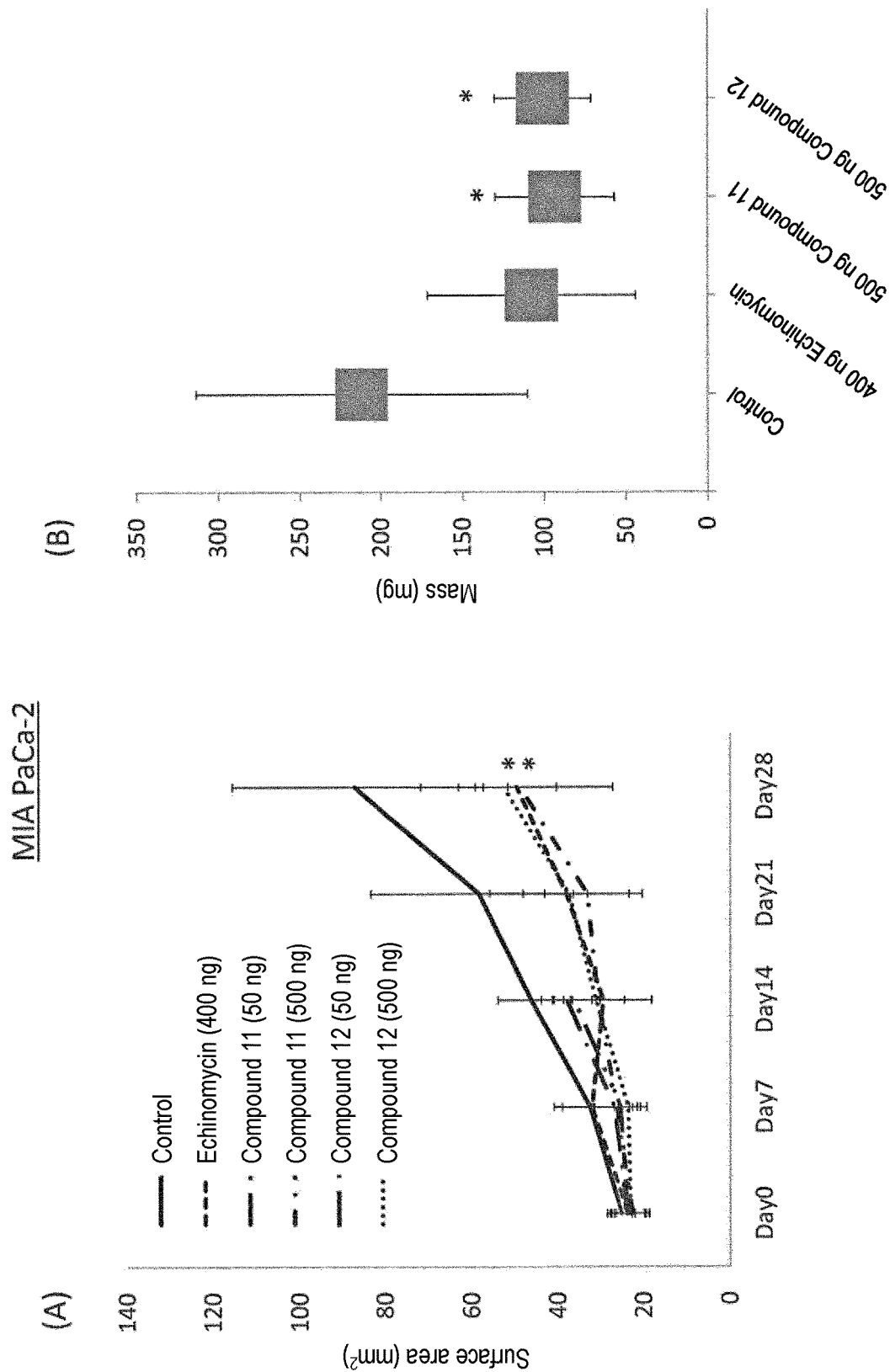
Figure 2:
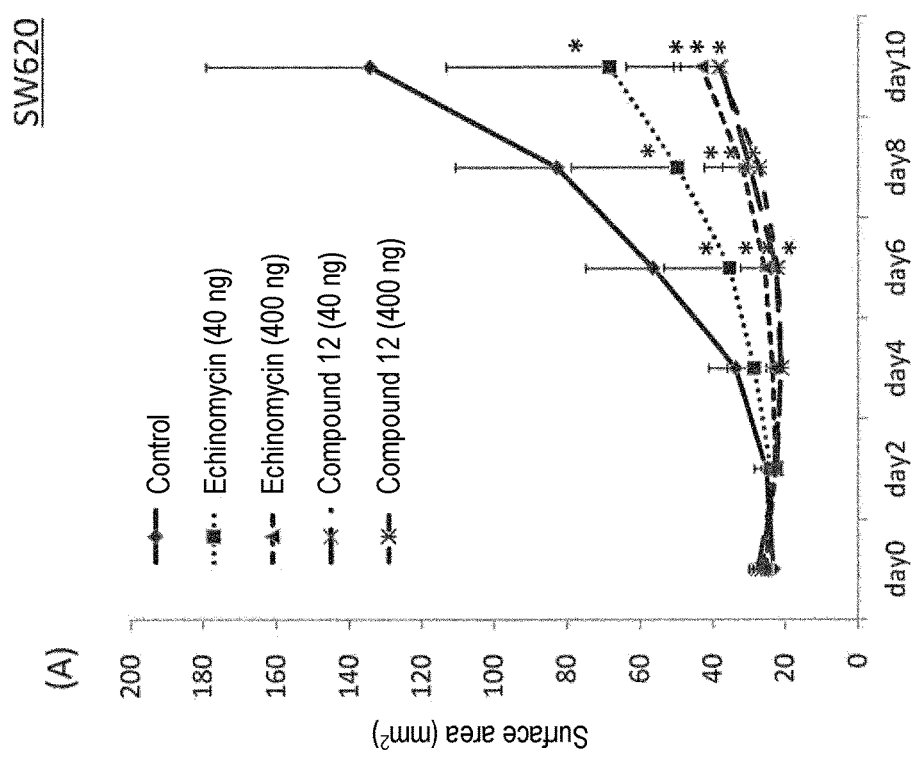
Figure 3:
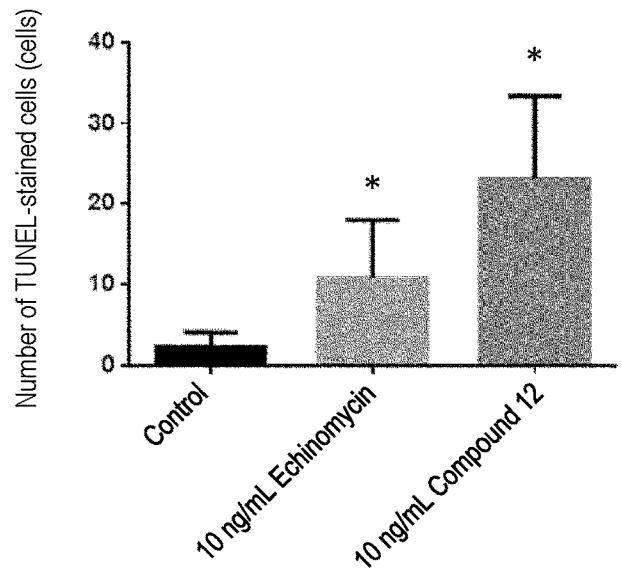

FIGS. 1-1 to 1-3 show results of the SRB assay.

A significant difference in absorbance was found between the control and the group with addition of 100 ng/mL or more of compound 12 for any of the cell lines, and the compound was confirmed to have activity to suppress the growth of cancer cells (FIGS. 1-1 to 1-3). It was found for the MIA PaCa-2 cell line and the SW620 cell line that the activity at a low concentration (10 ng/mL) is higher than that of echinomycin.

(Tumor-Cell-Transplanted Animal Model Assay 1—Evaluation on Size of Transplanted Tumor)

FIGS. 2-1 and 2-2 show results of Tumor-Cell-Transplanted Animal Model Assay 1—Evaluation on Size of Transplanted Tumor.

Reduction in the size of transplanted tumor was found for the case with administration of 500 ng of compound 11 (FIG. 2-1). This activity was confirmed to be comparable with that provided by administration of 400 ng of echinomycin.

In the case of compound 12, on the other hand, reduction in the size of transplanted tumor was found for any of the cell lines and any of the loadings (FIGS. 2-1 and 2-2). In particular, the effect of administration of 40 ng of compound 12 was confirmed to be comparable with that of administration of 400 ng of echinomycin.

(Cell Death Inducibility)

FIG. 3 shows results of counting the number of cells that underwent cell death through the TUNEL method.

The number of cells that underwent cell death induced by administration of compound 12 was found to be significantly larger than those for the control group and the group with administration of echinomycin (*: $p<0.05$ (vs control, Student's t-test)).

Figure 4:
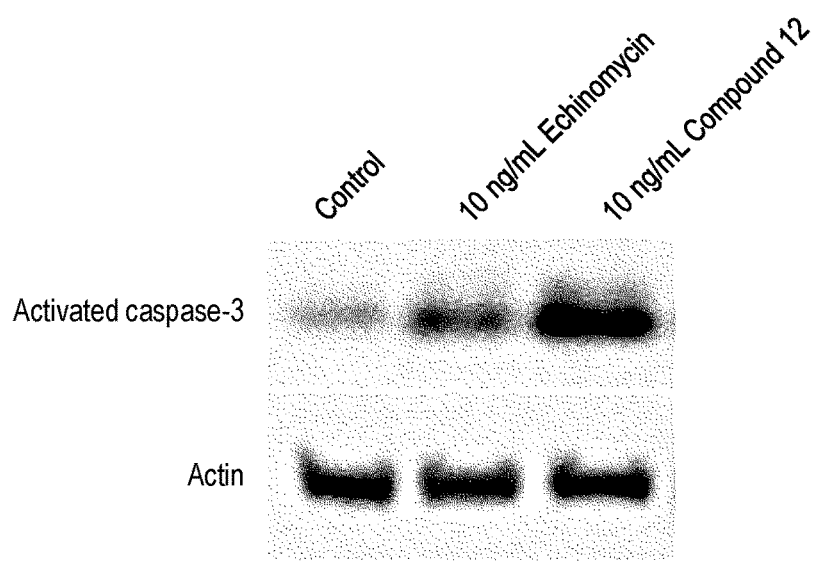
FIG. 4 shows results of evaluation on the cell death inducibility of the compound of the present invention for a colorectal cancer cell (SW620 cell) line through quantification (Western blotting) of activated caspase-3.

FIG. 4 shows results of quantifying activated caspase-3 through Western blotting.

The amount of activated caspase-3 was *1107±273 for the group with administration of compound 12, and confirmed to be larger than that for the control group (100±45) and that for the group with administration of echinomycin (*362±176) (*: $p<0.05$ (vs control, Student's t-test)). The numerical values shown for the group with administration of compound 12 and the group with administration of echinomycin are relative values to the numerical value for the control group.

These results demonstrate that compound 12 has higher cell death induction activity against tumor, in other words, higher anti-cancer activity than echinomycin.

(Tumor-Cell-Transplanted Animal Model Assay 2—Evaluation on Body Weight Variation)

Figure 5:
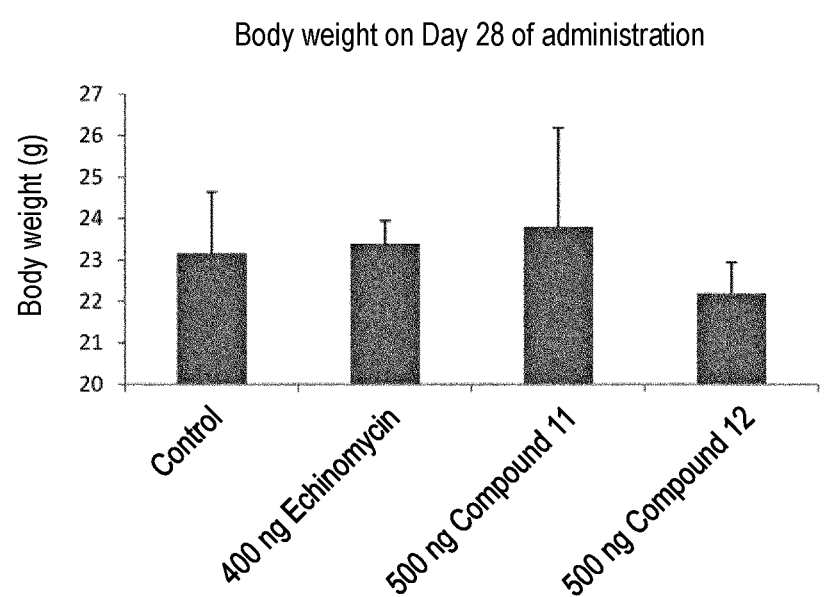
FIG. 5 shows a graph representing body weights of animal models with a pancreatic cancer cell line transplanted, where the compound of the present invention was administered to the animal models on each day, and the body weights are those measured on Day 28 of administration.

FIG. 5 shows body weights for the groups on day 28 of administration. Large reduction in body weight was not found for any of the group with administration of compound 11 and the group with administration of compound 12, as well as the control group and the group with administration of echinomycin. This result suggests that the compound of the present invention has low toxicity.

The above-described results reveal that the compound of the present invention can be produced by using a procedure of chemical synthesis, and has anti-cancer activity comparable with that of echinomycin, or higher than that of echinomycin.

The invention claimed is:

1. A compound or a salt thereof, the compound represented by formula (I):

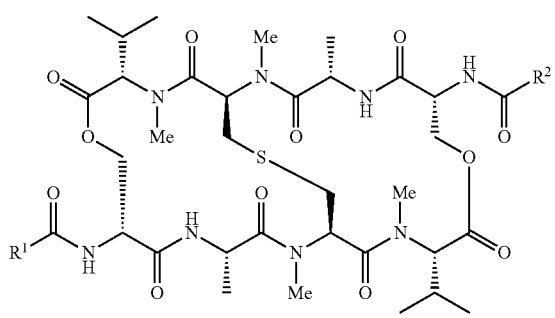

wherein $R^1$ and $R^2$ are each independently selectable and identical or different, and each represent an aromatic hydrocarbon group, saturated or unsaturated heterocyclic group, anthraquinone group, or benzophenone group optionally substituted with one or more substituents.

2. The compound or salt thereof according to claim 1, wherein $R^1$ and $R^2$ are each independently selectable and identical or different, and are each a group selected from a quinolyl group, an isoquinolyl group, a quinazolinyl group, a quinoxalyl group, a cinnolyl group, an indolyl group, a benzofuranyl group, a benzothiazolyl group, a benzoxazolyl group, a benzothiophene group, a pyrazyl group, an anthraquinone group, and a benzophenone group, and optionally substituted with one or more substituents selected from the group consisting of a hydrogen atom, a halogen atom, a hydroxy group, and a $C_{1-6}$ alkyl group.

3. The compound or salt thereof according to claim 1, wherein the compound is represented by formula (II):

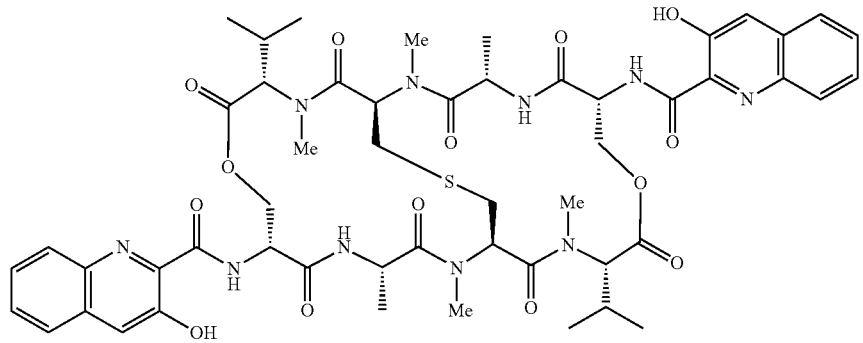 [SMILES: CC(C)[C@H]1C(=O)OC[C@@H](NC(=O)c2nc3ccccc3cc2O)C(=O)N[C@@H](C)C(=O)N(C)[C@H]2CSC[C@H](CN(C)C(=O)[C@H](C)NC(=O)[C@H](NC(=O)c3nc4ccccc4cc3O)COC(=O)[C@H](C(C)C)N(C)C2=O)C(=O)N1C]

or formula (III):

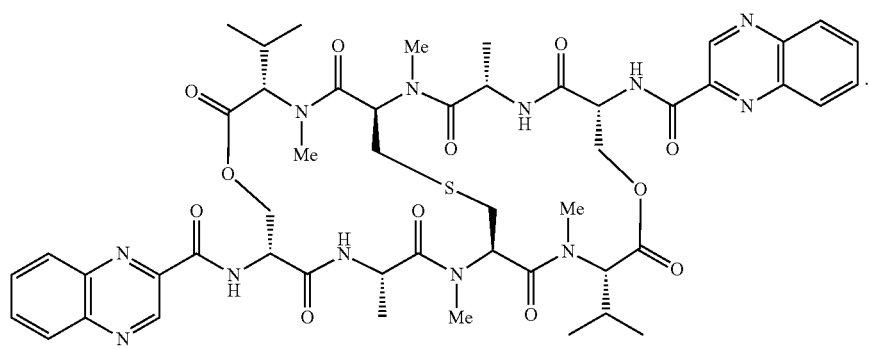 [SMILES: CC(C)[C@H]1C(=O)OC[C@@H](NC(=O)c2cnc3ccccc3n2)C(=O)N[C@@H](C)C(=O)N(C)[C@H]2CSC[C@H](CN(C)C(=O)[C@H](C)NC(=O)[C@H](NC(=O)c3cnc4ccccc4n3)COC(=O)[C@H](C(C)C)N(C)C2=O)C(=O)N1C]

4. A pharmaceutical composition comprising the compound or salt thereof according to claim 1.

5. A method for producing the compound according to claim 1, the method comprising:
a step of producing the compound represented by formula (I) from a compound represented by formula (6):

(Formula 6)

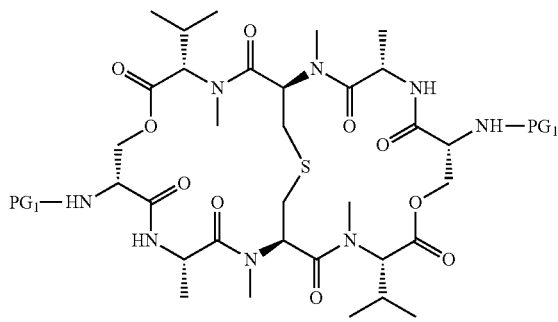

wherein $PG_1$ represents a protective group for an amino group, and compounds represented by formula (7):

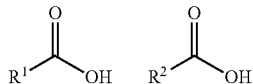
(Formula 7)

wherein $R^1$ and $R^2$ are each independently selectable and identical or different, and each represent an aromatic hydrocarbon group, saturated or unsaturated heterocyclic group, anthraquinone group, or benzophenone group optionally substituted with one or more substituents.

6. The method according to claim 5, wherein the compound represented by formula (6) is produced by reacting a compound represented by formula (3):

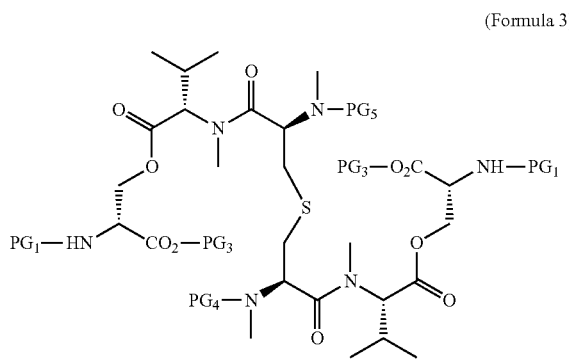
(Formula 3)

wherein $PG_1$ represents a protective group for an amino group, $PG_3$ represents a protective group for a carboxy group, and $PG_4$ and $PG_5$ are identical or different and each represent a protective group for an amino group, provided that $PG_4$ and $PG_5$ are different from $PG_1$, and a compound represented by formula (4):

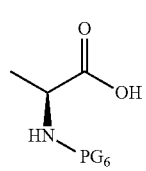
(Formula 4)

wherein $PG_6$ represents a protective group for an amino group, provided that $PG_6$ is different from $PG_1$, to produce a compound represented by formula (5):

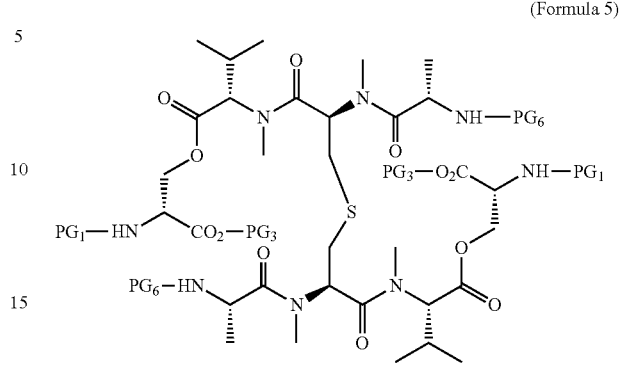
(Formula 5)

wherein $PG_1$, $PG_6$, and $PG_3$ are as defined above, and producing the compound represented by formula (6) from the obtained compound represented by formula (5).

7. The method according to claim 6, wherein the compound represented by formula (3) is produced from a compound represented by formula (1):

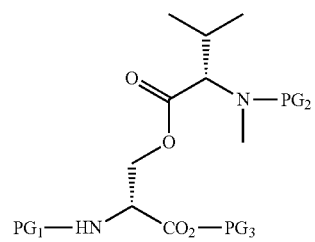
(Formula 1)

wherein $PG_1$ represents a protective group for an amino group, $PG_2$ represents a protective group for an amino group, provided that $PG_2$ is different from $PG_1$, and $PG_3$ represents a protective group for a carboxy group, and a compound represented by formula (2):

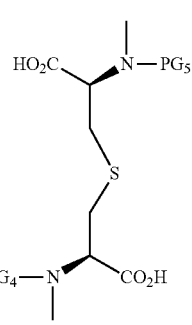
(Formula 2)

wherein $PG_4$ and $PG_5$ are identical or different and each represent a protective group for an amino group, provided that $PG_4$ and $PG_5$ are different from $PG_1$.

8. The compound or salt thereof according to claim 2, wherein the compound is represented by formula (II):

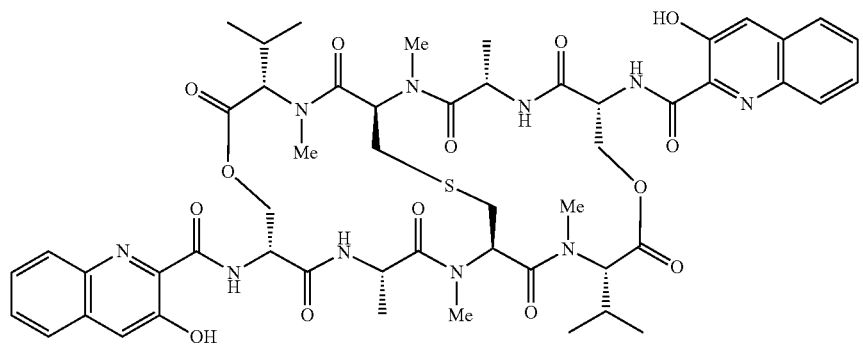 [SMILES: CC(C)[C@H]1C(=O)OC[C@@H](NC(=O)c2nc3ccccc3cc2O)C(=O)N[C@@H](C)C(=O)N(C)[C@H]2CSC[C@H](CN(C)C(=O)[C@H](C)NC(=O)[C@H](NC(=O)c3nc4ccccc4cc3O)COC(=O)[C@H](C(C)C)N(C)C2=O)C(=O)N1C]

or formula (III):

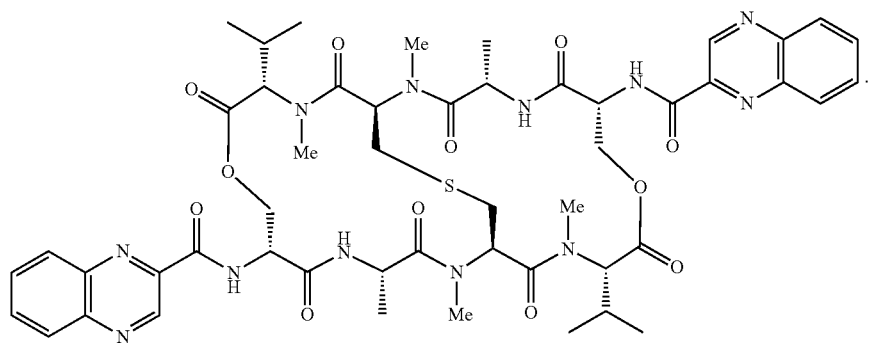 [SMILES: CC(C)[C@H]1C(=O)OC[C@@H](NC(=O)c2cnc3ccccc3n2)C(=O)N[C@@H](C)C(=O)N(C)[C@H]2CSC[C@H](CN(C)C(=O)[C@H](C)NC(=O)[C@H](NC(=O)c3cnc4ccccc4n3)COC(=O)[C@H](C(C)C)N(C)C2=O)C(=O)N1C]

9. A pharmaceutical composition comprising the compound or salt thereof according to claim 2.

10. A pharmaceutical composition comprising the compound or salt thereof according to claim 3.

11. A method for producing the compound according to claim 2, the method comprising:

a step of producing the compound represented by formula (I) from a compound represented by formula (6):

(Formula 6)

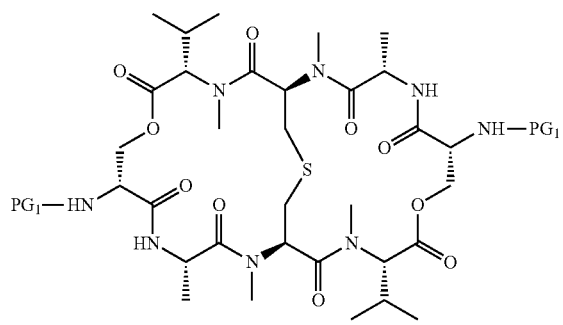

wherein PG₁ represents a protective group for an amino group, and compounds represented by formula (7):

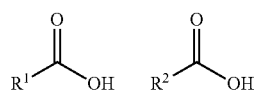

(Formula 7)

wherein $R^1$ and $R^2$ are each independently selectable and identical or different, and each represent an aromatic hydrocarbon group, saturated or unsaturated heterocyclic group, anthraquinone group, or benzophenone group optionally substituted with one or more substituents.

12. A method for producing the compound according to claim 3, the method comprising:

a step of producing the compound represented by formula (I) from a compound represented by formula (6):

(Formula 6)

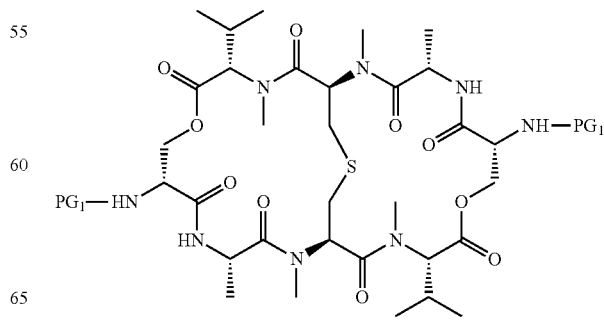

wherein $PG_1$ represents a protective group for an amino group,
and compounds represented by formula (7):

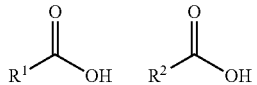

(Formula 7)

wherein $R^1$ and $R^2$ are each independently selectable and identical or different, and each represent an aromatic hydrocarbon group, saturated or unsaturated heterocyclic group, anthraquinone group, or benzophenone group optionally substituted with one or more substituents.

* * * * *